(12) United States Patent
Mateu et al.

(10) Patent No.: US 8,299,162 B2
(45) Date of Patent: Oct. 30, 2012

(54) LOW ENERGY, COLD PROCESS FORMULATION AID

(75) Inventors: Juan R. Mateu, Oak Ridge, NJ (US); Adam Perle, Saddle Brook, NJ (US)

(73) Assignee: Jeen International Corporation, Fairlawn, NJ (US)

( * ) Notice: Subject to any disclaimer, the term of this patent is extended or adjusted under 35 U.S.C. 154(b) by 0 days.

(21) Appl. No.: 13/082,317

(22) Filed: Apr. 7, 2011

(65) Prior Publication Data

US 2011/0250249 A1    Oct. 13, 2011

Related U.S. Application Data

(60) Provisional application No. 61/321,765, filed on Apr. 7, 2010, provisional application No. 61/347,664, filed on May 24, 2010, provisional application No. 61/435,128, filed on Jan. 21, 2011.

(51) Int. Cl.
| | |
|---|---|
| *C08J 3/22* | (2006.01) |
| *C08G 63/60* | (2006.01) |
| *C08G 73/10* | (2006.01) |
| *C08F 2/44* | (2006.01) |
| *B01F 3/12* | (2006.01) |
| *A61K 8/02* | (2006.01) |

(52) U.S. Cl. ........ 524/487; 524/599; 524/763; 524/845; 516/77; 424/401

(58) Field of Classification Search ........................ None
See application file for complete search history.

(56) References Cited

U.S. PATENT DOCUMENTS

| | | | |
|---|---|---|---|
| 2007/0092470 A1 | 4/2007 | Allef et al. | |
| 2008/0045916 A1* | 2/2008 | Herfert et al. ................. | 604/372 |
| 2008/0193405 A1 | 8/2008 | Mukherjee et al. | |
| 2008/0317686 A1 | 12/2008 | Mateu et al. | |

FOREIGN PATENT DOCUMENTS

WO    WO 00/62825    * 10/2000

* cited by examiner

*Primary Examiner* — Richard Schnizer
*Assistant Examiner* — Alma Pipic
(74) *Attorney, Agent, or Firm* — Louis C. Paul

(57) ABSTRACT

Provided are cold process formulation aids, methods for their manufacture, and personal care products made using them. The cold processing aids include a wax and a polymer having a backbone and a plurality of pendant groups thereon that are pendant ionic or ionizable groups, or pendant groups having at least one permanent dipole that includes an alcohol, thiol, ester, amide, imide, imine, or nitrile moiety. The backbone can be an aliphatic backbone, a polysaccharide backbone, a siloxane backbone, or a polyamide backbone. Also provided is a method of making personal care products using the cold processing aid.

5 Claims, No Drawings

LOW ENERGY, COLD PROCESS FORMULATION AID

CROSS-REFERENCES TO RELATED APPLICATIONS

This application claims the priority benefit of U.S. Provisional Application Ser. No. 61/321,765 filed on Apr. 7, 2010, U.S. Provisional Application Ser. No. 61/347,664 filed on May 24, 2010, and U.S. Provisional Application Ser. No. 61/435,128 filed on Jan. 21, 2011, the contents of which are incorporated herein by reference in their entirety.

STATEMENT REGARDING FEDERALLY SPONSORED RESEARCH OR DEVELOPMENT

Not applicable.

FIELD OF THE INVENTION

The present invention is directed to low-energy, low carbon footprint, cold process formulation aids, methods for their manufacture, and methods of using them in the manufacture of personal care products. An important characteristic of the cold process formulation aids of the present invention is that, when combined with an aqueous medium at a temperature not exceeding about 30° C., a hydrogel is formed. When the cold process aid of the present invention is combined with an aqueous medium and other ingredients, an emulsion can be formed. The emulsion can be of the oil-in-water type or, in certain embodiments, of the water-in-oil type.

SUMMARY OF THE INVENTION

The present invention relates to cold process formulation aids (CPFAs), methods for their manufacture, uses of CPFAs in making cold process emulsions and hydrogels for use in personal care, household and industrial applications. The cold processing aids include a wax and a polymer having a backbone and a plurality of pendant groups thereon that are pendant ionic or ionizable groups, or pendant groups having at least one permanent dipole that includes an alcohol, thiol, ester, amide, imide, imine, or nitrile moiety. The backbone can be an aliphatic backbone, a polysaccharide backbone, a siloxane backbone, or a polyamide backbone.

DETAILED DESCRIPTION OF THE INVENTION

As used herein, "aqueous medium" refers to a substance that is liquid at room temperature (22°-27° C.) and that includes at least 50%, preferably at least 75%, still more preferably at least 90%, by weight, water. The remainder of the aqueous medium can be compounds that are freely miscible with water, for example alcohols such as ethanol and the propanols, and polyalkylene glycols, to mention just a few.

The cold process formulation aid of the present invention, in certain of its embodiments, includes a polymer having an aliphatic backbone and a plurality of pendant groups thereon that are pendant ionic or ionizable groups, and/or that are pendant groups having at least one permanent dipole that includes an alcohol, thiol, ester, amide, imide, imine, or nitrile moiety.

By aliphatic backbone is meant that the main polymer chain consists of a majority, preferably essentially exclusively, of carbon-carbon bonds.

Polymers having an aliphatic backbone are well known in the polymer arts and can be made by, for example, free-radical initiated polymerization of compounds (monomers) having a carbon-carbon double bond, colloquially referred to as "vinyl-type monomers". Poly(methyl methacrylate) and poly(acrylic acid) are examples of polymers having aliphatic backbones that can be obtained by the free-radical polymerization of, respectively, methyl methacrylate and acrylic acid.

The polymers having an aliphatic backbone and a plurality of pendant groups thereon that are pendant ionic or ionizable groups, and/or that are pendant groups having at least one permanent dipole that includes an alcohol, thiol, ester, amide, imide, imine, or nitrile moiety useful in making the cold process formulation aid of the present invention can be homopolymers, obtained by polymerizing a single monomer, or they can be co- or ter-polymers, obtained by polymerizing a mixture of two or three monomers.

The polymers having an aliphatic backbone and a plurality of pendant groups can be, and in certain embodiments are, crosslinked polymers. Crosslinking can be achieved by methods known in the art, for example by combining a compound ("crosslinking agent") having two or more polymerizable carbon-carbon double bonds with the monomer(s) being polymerized. Allyl ether and $\alpha,\omega$-diallyl ethers and $\alpha,\omega$-diacrylate or dimethacrylate esters of poly(alkylene glycols) are examples of crosslinking agents that can be used to prepare crosslinked polymers having an aliphatic backbone and a plurality of ionic, ionizable, or permanent dipole-containing pendant groups. Others crosslinking agents are known in the art.

The pendant groups, occasionally referred to in the art as "side-chains", useful in the practice of certain embodiments of the present invention are groups, or "radicals", that are attached to a carbon atom in the main polymer chain by a chemical bond, but are not part of the main polymer chain. The pendant groups attached to the main polymer chain can be present in the monomer(s) at the time of polymerization, or they can be formed by post-polymerization reaction, for example post-polymerization salification or hydrolysis of a salifiable or hydrolysable functional group that was present as, or as part of, a substituent on the monomer(s) at the time of polymerization. The methoxycarbonyl [—C(O)—OCH$_3$] group of poly(methyl methacrylate), obtained by polymerization of methyl methacrylate, is an example of a pendant group that was present as a substituent on a monomer at the time of polymerization.

The pendant groups of the polymers having an aliphatic backbone and a plurality of pendant groups that are useful in the practice of certain embodiments of the present invention can be ionic or ionizable, or they can be groups that have at least one permanent dipole due to the presence in the pendant group of an alcohol, thiol, ester, amide, imide, imine, or nitrile moiety, or they can be a combination of any of the foregoing.

Ionic pendant groups carry permanent ionic charges. The carboxylate group, —C(O)O$^-$M$^+$, where M$^+$ is a metal cation, especially a cation of an alkali metal, is an example of an ionic pendant group. Sodium polyacrylate (the sodium salt of poly (acrylic acid)) is a preferred polymer having an aliphatic backbone and a plurality of pendant ionic groups for use in certain embodiments of the cold process formulation aid of the present invention.

Ionizable pendant groups are or include a functional group that includes, a labile ("acidic") hydrogen atom. The carboxyl group (—CO$_2$H), the sulfate group (—O—SO$_3$H), and the sulfite group (—SO$_3$H) are examples of functional groups that have labile hydrogen atoms and that can be, or be a constituent of, an ionizable pendant group. Polymers of acrylic acid, commonly referred to as "carbomers", are preferred polymers having an aliphatic backbone and a plurality of ionizable pendant groups that are useful in the cold process formulation aid of the present invention, in certain of its embodiments.

Pendant groups having a permanent dipole include pendant groups that are or that include one or more of an alcoholic hydroxyl group, thiolic thiol group, ester group, amide group, imide group, imine group, or nitrile group, to mention just a few. Examples of polymers having an aliphatic backbone and a plurality of pendant groups having a permanent dipole include poly(vinyl pyrrolidone), poly(vinyl alcohol), poly (methyl methacrylate), and copolymers of methyl acrylate and/or methyl methacrylate with alkyl esters of acrylic acid and/or methacrylic acid having about 10 to about 30 carbon atoms in the alkyl group, to mention just a few.

The plurality of pendant groups of the polymers having an aliphatic backbone and a plurality of pendant groups that are useful in the practice of the present invention, in certain of its embodiments, can include more than one type of pendant group selected, independently, from ionic, ionizable, and permanent-dipole-including pendant groups. To mention just one example, such polymer can have both alkyl ester and carboxyl pendant groups. Such polymer can also have more than one species of the same type or genus of pendant group. For example, such polymer can have both carboxyl and sulfate ionizable pendant groups, to mention just one example.

The cold process formulation aid of the present invention, in other of its embodiments, includes a polymer having a polysaccharide backbone and a plurality of pendant ionizable or ionic groups selected from carboxyl groups, sulfate groups, salts of either, or combinations thereof. The polysaccharide backbone can include either or both of pyranoside and furanoside residues. Important is that the polysaccharide backbone have a plurality of pendant ionizable or ionic groups selected from carboxyl groups, sulfate groups, salts of either, or combinations thereof. Preferred are polysaccharides that swell in water at room temperature, non-limiting examples of which include sodium alginate, carrageenan, carboxymethyl cellulose, xanthan, starches, and cationic guar.

The cold process formulation aid of the present invention, in other of its embodiments, includes poly(aspartate) or a salt thereof. Poly(aspartate) and its salts perform the same function as, and are claimed to be an even more eco-friendly alternative to, the polymers having an aliphatic backbone and a plurality of pendant groups thereon that are pendant ionic or ionizable groups and discussed above. Sodium poly(aspartate), frequently referred to in the trade as simply poly(aspartate), is particularly useful in the practice of the present invention.

In still further embodiments, the cold process formulation aid of the present invention includes a combination of one or more polymers having an aliphatic backbone and a plurality of pendant groups thereon that are pendant ionic or ionizable groups, one or more a polymer having a polysaccharide backbone and a plurality of pendant ionizable or ionic groups selected from carboxyl groups, carboxylate groups, sulfate groups, and salts thereof, and/or poly(aspartate).

One embodiment encompasses a cold process for making a hydrogel or an emulsion comprising the step of combining a cold process formulation aid having a wax component with an aqueous medium, at a temperature not exceeding 30° C., wherein the cold process formulation aid is in the form of a powder, a paste, or a semi-solid and consists essentially of: (i) a polymer having an aliphatic backbone and a plurality of pendant groups thereon that are pendant ionic or ionizable groups, and (ii) a self-emulsifying wax, the ratio, by weight of the self-emulsifying wax to the polymer having an aliphatic backbone and a plurality of pendant groups thereon that are pendant ionic or ionizable groups is from about 70:30 to 98:2.

Examples of polymers of the above-described types include polymers of acrylic acid, methacrylic acid or one of their esters. Other copolymers of acrylic acid useful in the practice of the present invention include ammonium VA/acrylates copolymer, sodium acrylates copolymer, ethylene/acrylic acid copolymer, ethylene/calcium acrylate copolymer, ethylene/magnesium acrylate copolymer, ethylene/sodium acrylate copolymer, ethylene/zinc acrylate copolymer, ethylene/acrylic acid/VA copolymer, acrylates/VP copolymer, acrylates/VA copolymer, steareth-10 allyl ether/acrylatescopolymer, acrylates/steareth-50 acrylate copolymer, acrylates/steareth-20 methacrylate copolymer, acrylates/ammonium methacrylate copolymer, styrene/acrylates copolymer, styrene/acrylates/ammonium methacrylate copolymer, 10 ammonium styrene/acrylates copolymer, sodium styrene/acrylates copolymer, acrylates/hydroxyesters acrylates copolymer, betaine acrylate copolymers including methacryloyl ethyl betaine/acrylates copolymer, lauryl acrylate/VA copolymer, VA/butyl maleate/isobornyl acrylate copolymer, ethylene/methacrylate copolymer, vinylcaprolactam/VP/dimethylaminoethyl methacrylate copolymer, sodium acrylates/acrolein copolymer, VP/dimethylaminoethylmethacrylate copolymer, AMP-acrylates copolymer), where "VA" is "vinyl acetate" and "VP" is "vinyl polymer".

Polymers of acrylic acid and its salts (polyacrylic acid, ammonium polyacrylate, potassium aluminum polyacrylate, potassium polyacrylate, sodium polyacrylate) have similar properties and can be used in the practice of the present invention.

Other copolymers copolymerized with polyacrylates include polyacrylamide and PVA, sodium polyacrylate starch, acrylamide/sodium polyacrylate, hydroxyethyl acrylate/sodium acrylodimethyl taurate copolymer, acrylate copolymer, acrylamide/ammonium acrylate copolymer, acrylates/beheneth-25 methacrylate/steareth-30 methacrylate copolymer, polyvinyl alcohols (and derivatives or blends), PVP (derivatives and blends), sodium/carbomer, carbomer, TEA-carbomer, and acrylates/C10-30 alkyl acrylate crosspolymer, to mention just a few.

Examples of commercially available polymers having an aliphatic backbone and a plurality of pendant groups thereon that are pendant ionic or ionizable groups, and/or that are pendant groups having at least one permanent dipole include Carbopols® Ultrez-10, Ultrez-20, Ultrez-21; Pemulen TR-1 and Pemulin TR-2 (all the foregoing available from Lubrizol Advanced Materials, Cleveland Ohio, USA); as well as Sepinov EMT-10 (distributed in the United States by SEPPIC Inc., Fairfield N.J.), to mention just a few.

In yet further embodiments, the cold process formulation aid of the present invention includes one or more polymers having a silicone backbone with pendant ionic or ionizable groups, and/or that are pendant groups having at least one permanent dipole that includes an alcohol, thiol, ester, amide, imide, imine, or nitrile moiety. Examples of such polymers include amodimethicone and dimethiconol, to mention just two.

Polymers having pendant ionic or ionizable groups can be referred to as polyelectrolytes.

The cold process formulation aid of the present invention, in all of its embodiments, includes at least one wax. Waxes are lipophilic fatty substances, which are solid or semi-solid at room temperature, that undergo a reversible solid-liquid change of state, with a melting point of greater than or equal to about 30° C., and up to about 150° C., and have an anisotropic crystal organization in solid form. Preferably, the wax has a melting point of 35° C. to 100° C. But waxes having a melting point>100° C. or waxes having a melting point at or below room temperature (e.g., cocoa butter) can be used in particular embodiments of the present invention.

The skilled artisan knows that waxes of commerce rarely have a sharp melting point such as exhibited by, for example, purified organic compounds, and that the melting point of a wax may vary depending on the test method used. The well-known technique of differential scanning calorimetry (DSC) can be used to determine the melting point of a wax. DSC can, for example, be performed using a 5 mg sample and a heating rate of 10° per minute. In this example, the temperature at which the melting endotherm shows a maximum deviation from baseline (i.e. the "peak temperature") is taken as the melting point. Industry standards have been developed for determining the melting point of certain types or classes of waxes and, where such are available, can be used.

Waxes useful in the practice of the present invention can be classified by source or chemical structure. Waxes useful in the practice of the present invention can be either hydrogenated (fully or partially) or non-hydrogenated natural waxes, such as those obtained from animal, botanical, or mineral sources, or they can be synthetic waxes. Some synthetic waxes are synthesized using one or more components from natural sources. Synthetic waxes can include more than one wax, each from a different source or of a different chemical class or structure, or they can be a natural wax that has been compounded with other components to obtain a synthetic wax.

Natural waxes that are animal waxes include beeswax, lanolin, shellac wax, and whale wax. Natural waxes that are botanical waxes include candelilla wax, castor wax, cotton wax, soy wax, jojoba wax, olive wax, carnauba wax, sugar cane wax, rice bran wax, bayberry wax, sunflower wax, rose petal wax, and Japan wax. Sunflower wax is a preferred botanical wax for use in the practice of certain embodiments of the cold process formulation aid of the present invention.

Mineral waxes include montan wax, ozokerite, and ceresin.

Petroleum-based waxes include paraffin wax and microcrystalline wax.

Synthetic waxes include polyethylene waxes (e.g. Jeenate® waxes available from Jeen International of Fairfield N.J., USA), silicone waxes, fluoro waxes, Fischer-Tropsch waxes, polypropylene waxes, esters of poly(ethylene glycol), and pegylated sorbitans, alone or in combination with, for example, monoalkyl ethers of poly(ethylene glycol) (e.g. ceteareth-20). Synthetic waxes also include pegylated animal waxes (e.g. PEG-8 beeswax).

In certain embodiments of the cold process formulation aid of the present invention, the wax is a synthetic emulsifying wax, for example glyceryl monostearate, to mention just one. Self-emulsifying wax, as that term is used herein, refers to a chemically modified wax that contains at least one emulsifier component, e.g., a non-ionic emulsifier.

The wax component of the self-emulsifying wax contains one or more cosmetically or dermatological acceptable waxes from among waxes of animal origin, waxes of plant origin, waxes of mineral origin and waxes of synthetic origin. Examples of waxes of animal origin include beeswaxes, lanolin waxes and Chinese insect waxes. Examples of waxes of plant origin include rice waxes, olive wax, carnauba wax, candellila wax, sugar cane waxes, Japan waxes, and cotton wax. Examples of waxes of mineral origin include paraffins, microcrystalline waxes, montan waxes and ozokerites. Examples of waxes of synthetic origin include polyolefin waxes, e.g., polyethylene waxes, waxes obtained by Fischer-Tropsch synthesis, waxy copolymers and their esters, and silicone and fluoro waxes.

Alternatively, hydrogenated oils of animal or plant origin (natural waxes) may be present in the self-emulsifying wax in combination with synthetic compounds. Thus, synthetic waxes useful in the practice of the present invention include substances that can include components from natural sources.

Waxes also include esters of long-chain primary alcohols and fatty acids, as well as shea butter and cocoa butter.

Self-emulsifying waxes may be obtained commercially from numerous manufacturers and suppliers. Commercially available self-emulsifying waxes that may be useful in the practice of the present invention include the following: PEG-20 sorbitan beeswax (Atlas G-1726, Uniqema; Nikkol GBW-125, Nikko), PEG-6 beeswax (ESTOL 375, Uniqema), PEG-8 beeswax (Apifil, Gattefosse), Olivem 1000 (Cetearyl Olivate, Sorbitan Olivate, from B&T SRL), PEG-12 beeswax and PEG-12 carnauba wax.

In certain embodiments, the wax—regardless of source or type—is micronized. That is, the wax is used in the form of particles having an average particles size, as determined by partice size analyzers known in the art, including those available from Malvern, of about 50μ or less. When micronized waxes are used, additional options for making the cold process formulation aid of the present invention, discussed below, can be used. Micronized waxes useful in the practice of the present invention include Ceridust® micronized poly (ethylene) (Clariant), Micropoly® micronized poly(ethylene) wax (Micro Powders, Inc.), Microease® micronized synthetic waxes (MicroPowders, Inc.), and Microcare® waxes (MicroPowders, Inc) that include natural waxes (e.g. carnauba wax), to mention just a few. Anticaking agents, such as silicas or a harder wax, can be added to a softer wax. Additionally, plasticizers (e.g., esters) may be added to the wax before micronization.

Differential scanning calorimetry demonstrates that the heat of disassociation of the wax component of the cold process formulation aid is different than the heat of disassociation of the cold process formulation aid itself, the latter being lower. This difference is important both in terms of sensorial properties and rheological profiles of the final commercial product (i.e., the emulsion or hydrogel). By way of non-limiting example, the viscosity of an emulsion containing a wax (W) and polymeric thickener (P) formed by conventional processes (i.e., heating) is lower than the viscosity of an emulsion formed without heat (i.e., at room temperature) by adding a cold process formulating aid (WP) consisting essentially of the same wax and same polymeric thickener at the same concentrations as used in the conventional (i.e., heated) emulsion.

The cold process formulation aid of the present invention can be obtained in powder form, a preferred physical form, by combining one or more polymers having an aliphatic backbone and a plurality of pendant groups thereon that are pendant ionic or ionizable groups, one or more polymers having a polysaccharide backbone and a plurality of pendant ionizable or ionic groups selected from carboxyl groups, carboxylate groups, sulfate groups, and salts thereof, or poly(aspartate), or a combination of the foregoing, with at least one wax in a spray drying (also known as spray congealing when heat, rather than a solvent, is being removed), jet milling or prilling process. If the wax is a micronized wax micronized to an average particle size of about 5μ, a dry blending process can suffice.

In the spray drying process, the one or more polymers having an aliphatic backbone and a plurality of pendant groups thereon that are pendant ionic or ionizable groups, the one or more polymers having a polysaccharide backbone and a plurality of pendant ionizable or ionic groups selected from carboxyl groups, carboxylate groups, sulfate groups, and salts thereof, the poly(aspartate), or a combination of the foregoing are combined with one or more molten waxes at 30° C. to 150° C. and the combination converted to a powder by spray congealing.

The technique of spray-drying is well known in chemical engineering and is summarized, for example, in R. P. Patel et al., 2 *Indian Journal of Science and Technology*, Vol. No. 2, 44-48 (2009). The skilled artisan knows to adjust the temperature of the molten wax, the nozzle orifice size, and the atomizing pressure to obtain the desired particle size in the final powder product. Preferred particle sizes are in the range of 5μ to 5 mm, more preferably 5μ to 50μ.

Prilling is likewise a technique for forming particulate or granular solid particles and is well known in chemical engineering. Prilling is accomplished in a prilling tower in which droplets of a molten combination of one or more waxes with polymers having an aliphatic backbone and a plurality of pendant groups thereon that are pendant ionic or ionizable groups, one or more polymers having a polysaccharide backbone and a plurality of pendant ionizable or ionic groups selected from carboxyl groups, carboxylate groups, sulfate groups, and salts thereof, poly(aspartate), or a combination of the foregoing, are allowed to fall under the action of gravity through the tower against a static or dynamic column of gas, for example air or nitrogen. The height of the prilling tower, the temperature of the gas, and the size of the droplets are adjusted, by routine experimentation, according to the melting point of the wax and the desired size of the final prill.

The cold process formulating aids of the present invention may vary in physical forms ranging from coarse powder to flake and pastille, which, in turn, can be further reduced in size using a jet mill.

When the wax is not a micronized wax and the cold process formulation aid of the present invention is made by spray drying or prilling, the ratio, by weight, of the one or more waxes to the one or more polymers (i.e. the one or more polymers having an aliphatic backbone and a plurality of pendant groups thereon that are pendant ionic or ionizable groups, the one or more polymers having a polysaccharide backbone and a plurality of pendant ionizable or ionic groups selected from carboxyl groups, carboxylate groups, sulfate groups, and salts thereof, the poly(aspartate), or a combination of the foregoing) is preferably from about 60:40 to 80:20.

When a micronized wax having an average particle size not exceeding about 50μ is used, the cold process formulation of the present invention can be made by a dry blending process. In this case, the ratio, by weight, of one or more waxes to the one or more polymers is from about 85:15 to about 98:2. The dry blending can be accomplished using a ribbon mixer, a twin-shell mixer or a high intensity mixer.

The cold process formulation aid made by any of the above-described methods is preferably in the form of an easily-handled powder. However, the cold process formulation aid of the present invention, in certain embodiments, can also be provided in the form of a paste or a semi-solid having a butter-like consistency. When a paste form is desired, waxes having a melting point near or below room temperature, e.g. shea butter or especially cocoa butter, are included in the formulation, especially in combination with other waxes (e.g. beeswax). The cold process formulation aid of the present invention in paste form can be made using conventional compounding equipment, for example a Banbury mixer.

In still further embodiments, the present invention provides a cold process for making personal care products that includes the step of combining the cold process formulation aid of the present invention with an aqueous medium and other ingredients.

Additional ingredients that may be added to emulsions formed with the cold process formulation aids of the present invention include, but are not limited to, oils and esters (as plasticizers); iron oxides; capric caprylic triglyceride; glycerine; emulsifiers (polysorbate); silicone compounds, including volatile silicones, elastomers and resins silicone crosspolymer (Dow Corning 9506).

In another embodiment, the present invention provides a method of making a personal care product, without heating, that includes the steps of (i) combining with an aqueous medium, at a temperature not exceeding 30° C., a polymer having an aliphatic backbone and a plurality of pendant groups thereon that are pendant ionic or ionizable groups, or pendant groups having at least one permanent dipole that includes an alcohol, thiol, ester, amide, imide, imine, or nitrile moiety, thereby forming a hydrogel and (ii) adding a micronized wax, having a mean particle size from 5 to 50 microns, to the hydrogel of step (i).

Polymers having a polysaccharide backbone and a plurality of pendant ionizable or ionic groups selected from carboxyl groups, carboxylate groups, sulfate groups, and salts thereof, or polyaspartate can be substituted for the polymer having an aliphatic backbone in the above process.

As is known in the dermatologic arts, surfactants can be irritating or negatively impact active ingredients (e.g., by denaturing proteins). In a still further embodiment, the cold process formulation aid of the present invention provides a method of making a personal care product that is essentially free of ethoxylated surfactants, and in certain embodiments essentially of free of surfactants. By "essentially surfactant-free" is meant that no surfactant is added to the emulsion, other than surfactant(s), if any, present in the CPFA itself.

The present invention, in certain of its embodiments, is illustrated by the following non-limiting examples.

Example 1

First Process for Making a Cold Process Formulation Aid with Non-Micronized Wax and a Polyelectrolyte Polymer Non-micronized wax and an oil are melted together. A polyelectrolyte polymer having an aliphatic backbone and a plurality of pendant groups thereon that are pendant ionic or ionizable groups, or pendant groups having at least one permanent dipole that includes an alcohol, thiol, ester, amide, imide, imine, or nitrile moiety is combined with the molten wax. The polyelectrolyte polymer constitutes about 30% by weight of the combination. The combination is then cooled to a continuous solid mass and comminuted to the desired particle size.

In a modification of the first process, the molten combination of wax and polyelectrolyte polymer is not cooled to a continuous solid mass. Instead, the molten combination is passed through a spray drying apparatus to cool and spray congeal the combination to a powder.

In another modification of the first process, the molten combination is passed through a prilling tower to cool the combination and obtain a prin.

Example 2

Second Process for Making a Cold Process Formulation Aid with a Micronized Wax and a Polyelectrolyte Polymer Wax is micronized by jet mill pulverization to an average particle size of about 5µ. The micronized wax is dry blended with a polyelectrolyte polymer having an aliphatic backbone and a plurality of pendant groups thereon that are pendant ionic or ionizable groups, or pendant groups having at least one permanent dipole that includes an alcohol, thiol, ester, amide, imide, imine, or nitrile moiety to obtain the cold processing aid. The polymer having an aliphatic backbone and a plurality of pendant groups thereon that are pendant ionic or ionizable groups, or pendant groups having at least one permanent dipole that includes an alcohol, thiol, ester, amide, imide, imine, or nitrile moiety constitutes about 5% by weight of the dry-blended combination.

Example 3

Third Process for Making a Cold Process Formulation Aid Using a Non-Micronized Wax, a Polyelectrolyte Polymer, and a Silicone Crosspolymer Wax and a polyelectrolyte polymer (described in the previous examples) are melted together. Dow DC 9506 (a silicone cross polymer) is combined with the molten wax and the polyelectrolyte polymer. The molten combination is cooled to obtain a continuous solid mass that is comminuted to the desired particle size.

In a modification of the third process, the molten combination of wax, polyelectrolyte, polymer and silicone crosspolymer is not cooled to a continuous solid mass. Instead, the molten combination is passed through a spray drying apparatus to cool and spray congeal the combination to a powder.

In another modification of the third process, the molten combination is passed through a prilling tower to cool the combination and obtain a prill.

Example 4

Fourth Process for Making a Cold Process Formulation Aid

In a fourth process, a molten combination of polyelectrolyte and wax is further combined with oil phase ingredients (esters, natural oils, synthetic oils, butters (e.g., partially hydrogenated vegetable oils), silicone compounds) and/or hydrophilic ingredients (e.g., glycols) to make a paste or slurry, optionally with a surfactant. Two non-limiting examples of this process are as follows: (1) combine Beewax with Sodium Acrylate/Sodium Acryloyldimethyl Taurate Copolymer, Isohexdecane and Polysorbate 80; (2) combine Sunflower wax with Hydroxyethylacrylate/Sodium Acryloyldimethyl Taurate Copolymer.

Any of the above-mentioned processes may comprise the further step of pre-hydrating the cold process formulation aid of the present invention (i.e., by adding water).

Examples 5-15

Cold Process Formulation Aids

Example 5

Polyethylene (70%); Sodium Polyacrylate (30%)

Example 6

Sunflower Wax (70%); Sodium Polyacrylate (30%)

Example 7

Yellow Beeswax (70%); Sodium Polyacrylate (30%)

Example 8

Cocoa Butter PPP (35%); Yellow Beeswax (35%); Sodium Polyacrylate (30%)

Example 9

Polyethylene (45%); Polyvinylpyrrolidone (25%); Sodium Polyacrylate (30%)

Example 10

Stearic Acid (30%); Ceteareth-20 (7%); Cetearyl Alcohol (62%); Sodium Polyacrylate (1%)

Example 11

Stearic Acid, (32%); Cetearyl Alcohol (32%); Glyceryl Stearate (21%); Peg-100 Stearate (10%); Sodium Polyacrylate (5%)

Example 12

Cetearyl Alcohol (70%); Polysorbate 60 (25%); Sodium Polyacrylate (5%)

Example 13

Cetyl Alcohol (50%); Sodium Acrylate Acryloyl Dimethyl Taurate Copolymer (30%); Glyceryl Monostearate (15%); Caprylic/Capric Triglyceride (5%)

Example 14

Stearic Acid (99%); Sodium Acrylate Acryloyl Dimethyl Taurate Copolymer (1%)

Example 15

Sunflower wax (35%); Shea butter (35%); Sodium Polyacylate (30%)

Example 16

Polyethylene (35%); Sodium Polyacrylate (30%); Iron Oxides (15%); Titanium Dioxide (20%)

Example 17

Polyethylene (50%); Sodium Polyacrylate (30%); Dimethicone/Vinyl Dimethicone Crosspolymer (20%)

Example 18

Sunflower Wax (70%); Acrylates/C$_{10-30}$ Alkyl Acrylate Crosspolymer (30%)

Example 19

Sunflower wax (50%); Caprylic/Capric Triglyceride (20%); Guar Gum (30%)

Example 20

Sunflower wax (50%); Caprylic/Capric Triglyceride (20%); Carrageenan (30%)

Example 21

Sunflower wax (50%); Caprylic/Capric Triglyceride (20%); Sodium Alginate (30%)

The ratios of the component parts of the CPFAs (i.e., polymeric backbone, synthetic or natural, and wax) vary depending on the type of wax and the manufacturing process (e.g., jet milling). Dry blended CPFAs, irrespective of whether the wax is functionalized, can have ratios of as low as 0.5% polymer. Molten CPFAs containing emulsifying waxes (e.g., fatty acids, fatty alcohols) can also have as low as 0.5% polymer content. Molten CPFAs containing non-emulsifying waxes can have 20% or higher polymer content.

Example 22

Swollen Silicone Oil Gel

The cold process formulation aid of Example 3 is dispersed in water in a suitable vessel at a temperature not above about 30° C. When the processing aid is dispersed, the desired amount of silicone oil is added at a temperature not exceeding about 30° C. to obtain a gel swollen with the silicone oil.

Applications Examples

When mixed with an aqueous medium at a temperature not exceeding 30° C., the cold process formulation aid of the present invention forms a hydrogel or an emulsion. It is also possible to form an emulsion or hydrogel by adding the cold process formulation aid of the present invention at temperatures that do not exceed the melt point of the wax component of the cold process formulation aid or the melt point of the cold process formulation aid itself.

Mascaras

Certain embodiments of the present invention are directed to mascaras that enhance the volume or thickness of eyelashes. In particularly preferred embodiments, mascara compositions comprising the cold formulation processing aid of the present invention not only have long wear and curl, but also exhibit less clumping (i.e., on application and over time) and are easily removed (i.e., with water).

In addition to the cold process formulation aid of the present invention, the mascara compositions may contain one or more of (i) a self-emulsifying wax, (ii) a latex polymer, preferably copolymers of a (meth)acrylic acid and its esters or acrylates copolymers, (iii) film-forming polymers, water-soluble and/or oil-soluble, (iv) water-soluble thickening or gelling agents, and fibers.

Non-limiting examples of water-soluble, film-forming polymers include: polyacrylates and polymethacrylates; acrylates copolymers such as those sold by The Lubrizol Corp. under the tradename Avalure® AC and by Interpolymer under the Syntran® PC tradename (Syntran® PC 5208—Polyacrylate-15; Syntran® PC 5205/5227—Polyacrylate-15 (and) Polyacrylate-17; 3; Syntran® PC 5117—Polyacrylate-18 (and) Polyacrylate-19; Syntran® PC 5100 Polyacrylate 21 (and) Acrylates/Dimethylaminoethyl Methacrylate Copolymer; Syntran® PC 5400 Ammonium Acrylates); polyvinyl acetates; polyvinyl alcohols; cellulose derivatives (e.g., hydroxymethyl cellulose, sodium carboxymethylcellulose, ethyl cellulose, hydroxyethyl-cellulose, hydroxypropyl cellulose, and hydroxypropyl methylcellulose); cellulose acetate phthalate aqueous dispersion; polymers of chitin or chitosan; vinyl polymers, including vinyl pyrrolidone, polyvinylpyrrolidone (PVP) and copolymers of vinyl pyrrolidone and PVP (e.g., vinylpyrrolidone/acrylates/lauryl methacrylate copolymer, acrylates/C$_{1-2}$ succinates/hydroxyacrylates copolymer; PVP/DMAPA acrylates copolymer; copolymers of vinylpyrrolidone and caprolactam; polyurethanes (e.g., Polyurethane-1, a mixture of 30% polyurethane, 10% ethanol, and 60% water, sold under the tradename Luviset® P.U.R. by BASF, Aktiengesellschaft); polyester-polyurethane aqueous dispersions, such as those sold by The Lubrizol Corp. under the trade names Avalure® UR and Sancure®; and quaternized polymers (e.g., Syntran® PC 5320—Polyquaternium sold by Interpolymer).

Non-limiting examples of oil-soluble, film-forming polymers include hydrogenated polyisobutenes, polydecenes, adipic acid/diethylene glycol/glycerin crosspolymer, polyethylene, polyvinyl laurate, dienes (in particular, polybutadiene and cylopentadiene), and synthetic-terpene based resins.

Water-soluble thickening or gelling agents may be film-forming polymers and include: polyacrylamides such as Sepigel 305 (INCI name: polyacrylamide/C$_{13-14}$ isoparaffin/ Laureth 7) or Simulgel 600 (CTFA name: acrylamide/sodium acryloyldimethyltaurate copolymer/isohexadecane/polysorbate 80); polyvinylpyrrolidone (PVP); polyvinyl alcohol; crosslinked acrylates, such as crosslinked poly(2-ethylhexyl acrylate), and hydrophobically-modified acrylates; cellulose derivatives (illustrated above), polysaccharides and gums; and crosslinked methacryloyloxyethyl-trimethylammonium chloride homopolymers sold under the name Salcare SC95.

In preferred embodiments, the mascara contains both a water-soluble, film-forming polymer and an oil-soluble, film-forming polymer, where the water-soluble, film-forming polymer is present at a concentration of from 0.5% to 25%, preferably from 1% to 15%, still more preferably from 1% to 10%, and where the oil-soluble, film-forming polymer is present at a concentration of from 1% to 45%, preferably from 3% to 20%.

In mascara embodiments containing fibers, the fibers may be of natural origin (cotton, silk, wool) or synthetic (polyester, rayon, nylon or other polyamides). Fibers typically have an average length ranging from 0.5 mm to 4.0 mm, and preferably have an average length ranging from 1.5 mm to 2.5 mm. When present, fibers may comprise from 0.5% to 10% wt/wt, preferably from 1% to 5% wt/wt.

In other embodiments directed to volumizing hair fibers, in particular eyelashes, the composition may include particles, including powders of the present invention, that are initially at least about 5 microns in equivalent diameter or that prior to upon application to the lashes swell to a size of at least about 5 microns in equivalent diameter by any chemical or physical means.

One embodiment of the present invention is directed to volumizing eyelashes in a two-step process, first by applying a basecoat mascara followed by separate application of a topcoat mascara. The basecoat contains CPFAs of the present invention and is exemplified by the following formula: CPW-2 (Polyethylene, Sodium Polyacrylate)—10%; CPW-S (Sunflower wax, Sodium polyacrylate)—5%; Isododecane (40%); Mica 5%; CPW-5 (Polyethylene, Sodium Polyacrylate)—12%); Black Iron Oxide (8%); Jeelux VHIPP (Isopropyl Palmitate, Bis-vinyl Dimethicone/Dimethicone Copolymer)—25%. The topcoat is exemplified by the following formulation: Water—60%; PEG 150 —5%; DC 200 1.5 cst (Dimethicone) 25%; Avalure® UR 450 (PPG-17/IPDI/DMPA copolymer)—10%.

Self-Tanners/Autobronzers

Self-tanning formulations containing cold process formulation aids of the present invention include dihydroxyacetone and at least one reducing sugar, preferably and preferably also include a high molecular weight cationic polymer, preferred examples of the latter being described in the following U.S. patents, the disclosures of which are incorporated, in pertinent part, by reference: U.S. Pat. Nos. 4,599,379; 4,628,078; 4,835,206; 4,849,484; and 5,100,660. Erythrulose a $C_4$-keto-sugar (1,3,4-trihydroxy-butan-2-one) is a preferred reducing sugar and can be used in D- or L-form or also as the racemate. Other reducing sugars having self-tanning properties that can be used in combination with erythrulose include glucose, xylose, fructose, reose, ribose, arabinose, allose, tallose, altrose, mannose, galactose, lactose, sucrose, erythrose and glyceraldehyde.

Topical Anti-Aging and Dermatologic Compositions

Emulsions made with CPFAs of the present invention provide advantages over conventional emulsions made by heating two discontinuous phases and then mixing the two phases at elevated temperature until homogenous. Notably, temperature-sensitive active ingredients (those whose activity is negatively impacted, i.e., diminished, at elevated temperature and fragrances can be added directly to the cold process emulsion.

Emulsions containing CPFAs of the present invention can include a multitude of anti-aging skin care active ingredient. By "anti-aging skin care active ingredient" is meant an ingredient that helps to reduce the appearance of and/or prevent the formation of fine lines, wrinkles, age spots, sallowness, blotchiness, redness, dark circles (i.e., under the eyes). Anti-aging skin care active ingredients are also understood as helping to reduce skin oiliness, reduce transepidermal water loss, improve skin retention of moisture and/or improve skin elasticity. Non-limiting examples of skin care actives include: anti-inflammatory agents (e.g., 1,3 1,6 beta glucan; poly-glutamic acid (and) polyfructose); humectants; skin bleaching/lightening agents (e.g., hydroquinone, kojic acid, ascorbic acid, magnesium ascorbyl phosphate, ascorbyl 3 aminopropyl phosphate, ascorbyl 3 aminopropyl dihydrogen phosphate); skin soothing agents (e.g., panthenol and derivatives, aloe vera, pantothenic acid and its derivatives, allantoin, bisabolol, and dipotassium glycyrrhizinate); antioxidants; vitamins and derivatives thereof; exfoliants (e.g., abrasive particles, hydroxy-acids); anti-aging ingredients, including short-chain peptides (e.g., having less than about 12 amino acids); and self-tanning agents (e.g., dihydroxyacetone).

Reduction in the appearance of fine lines and wrinkles can be measured by a number of techniques known to those of skill in the art and including clinical assessment by a trained observer (e.g., doctor, nurse, technician) instrumentally (e.g., by use of Silflo replica masks or an imaging system such as VISIA from Canfield Scientific.) Improvements in elasticity are measurable, for example, with a Twistometer. Reduction in the rate of transepidermal water loss and improvement in skin moisture content are measurable, respectively, with an evaporimeter and corneometer.

In embodiments of the present invention where the cold process formulating aid is used to form a topical composition applied to skin exhibiting visible signs of aging (including fine lines, wrinkles, skin laxity, uneven pigmentation), acne lesions, psoriasis, rosacea or an inflammatory dermatosis, the composition may also contain a natural or synthetic analog of vitamin A (i.e., a "retinoid") including geometric isomers and stereoisomers, and includes the following compounds: retinol; retinal; $C_2$-$C_{22}$ alkyl esters of retinol; including retinyl palmitate, retinyl acetate, retinyl propionate; retinoic acid (including all-trans retinoic acid and/or 13-cis-retinoic acid); as well as compounds described as retinoids in U.S. Pat. Nos. 4,677,120; 4,885,311; 5,049,584; and 5,124,356.

In addition to the cold process formulation aids of the present invention, cosmeceutical compositions that reduce the appearance of the visible signs of aging, topical compositions applied in the treatment of acne and other inflammatory dermatoses, as well as self-tanning compositions (described above), may contain hydroxy acids, alpha hydroxy acids (AHAs). As used in the present application, AHAs conform to the formula $(R_1)(R_2)C(OH)COOH$ where $R_1$ and $R_2$ may be the same or different, and are selected from the group consisting of H, F, C, Br, alkyl, aralkyl, or aryl having 1-29 carbon atoms. The alkyl, aryl or aralkyl groups may be straight, branched or cyclic. $R_1$ and $R_2$ may be further substituted with OH, CHO, COOH or a $C_{1-9}$ alkoxy group. Additionally, beta hydroxyacids and polyhydroxyacids may also be added to topical compositions according to the present invention.

Hair Care Products

Cold process emulsions or hydrogels formulated in accordance with the present invention include hair care actives known to those of skill in the art that moisturize, condition, improve bending modulus, increase tensile strength, increase sheen/shine, improve touchability, reduce split ends, volumize, reduce fly-away, and/or increase longevity of color treatment. Such materials include proteins and polypeptides and derivatives thereof, antioxidants, humectants and moisturizing and conditioning agents Antiperspirant/Deodorants; Wet Wipes In another embodiment, the CPFA of the present invention is advantageously employed in a process for making an extrudable antiperspirant/solid stick at temperatures below the melting point of the formula. In this process, a homogenized mixture of CPFA, an antiperspirant and/or deodorant ("AP/Deo") active ingredient (for example, a salt or complex of aluminum and/or zirconium), a structurant (e.g., fatty alcohols and other waxes), absorbent/drying agents (especially, talc, clay, starches), volatile silicone(s), and, optionally, one or more of suspending agents, emollients, and fragrance are mixed and homogenized to achieve a desired consistency and feel. The resulting mixture is extruded to obtain a uniform, solid, cohesive extrudate that is cut to a desired length.

The above process is further illustrated by the following non-limiting example formulation. The AP/Deo active ingredient is incorporated by premixing the active with water and possibly a small amount of propylene glycol. Absorbent/drying agents are particles 10 microns or less and are present in amount of from about 8 to 20% wt/wt. The volatile silicone(s) are present at a least 15% wt/wt. Transparent AP/Deo sticks can be achieved by forming an emulsion incorporating CPFAs of the present invention, particularly self-emulsifying CPFAs (e.g., those including one or more emulsifiers such as PEG-100 Stearate, Polysorbate-60, Glyceryl Stearate), and oil phase ingredients where the refractive indices of the oil and water phase are adjusted to within 0.0005 to 0.001 units at room temperature.

A natural deodorizing powder may be prepared by mixing alum, sodium bicarbonate, waxes of essential oil and CPFAs formed from natural waxes and sodium polyacrylate (or one or more salts of sodium polyacrylate or both).

Low-viscosity AP/Deo roll-ons or sprays (viscosity of less than about 2,500 mPas) can be formulated with self-emulsifying CPFAs of the present invention as defined in the preceding paragraph. A non-limiting example of such a low-viscosity AP/Deo composition contains ## to ##% CPFAs of the present invention, 1% to 10% wt/wt, two glucosides in a concentration of from 2% to 10% wt/wt, polyglycerol-2-dipolyhydroxystearate at a concentration of from 5% to 8% wt/wt, about 5% wt/wt of a polyol, with the balance of the composition being oil components selected from the group of linear hydrocarbons with a chain length of 8 to 40 carbon atoms, esters, particularly esters formed by the reaction of $C_6$-$C_{24}$ fatty acids with $C_6$-$C_{24}$ fatty alcohols, Guerbet alcohols based on $C_6$-$C_{18}$ fatty alcohols, and silicone compounds. The esters and linear hydrocarbons may be branched or unbranched, saturated or unsaturated. In addition to use as roll-ons, sprays, the above-described composition may be used as an impregnating liquid for wet wipes.

Transfer-Resistant Colored Makeup Compositions

In one embodiment, the present invention is directed to a process for limiting and/or preventing the transfer of a colored make-up composition from the lips or the skin, where the colored make-up composition is comprised of a CPFA of the present invention, at least partially crosslinked, elastomeric organopolysiloxane, a fatty phase containing at least one oil that is volatile at room temperature. Transfer resistant lipsticks preferably include a siloxysilicate polymer, preferably trimethylsiloxy silicate. The colored make-up composition may be in the form of a foundation, a blush, an eyeshadow, a concealer, a lipstick, a lipstick topcoat (i.e., applied over a base lipstick), and a tinted moisturizer, preferably containing UV radiation absorbers or blocks. Tests for transfer-resistance are known to those of skill in the art and include the "Kiss Test" described in Example 4 of U.S. Pat. No. 5,505,937.

Additional Cosmetic Ingredients

As will be appreciated by persons skill in the art, a wide-range of water-immiscible materials may be added to the cold process emulsions of the present invention, non-limiting examples of which include (i) non-volatile silicone fluids, preferably have a viscosity ranging of from about 20 to 100,000 centistokes at 25° C.; (ii) nonvolatile hydrocarbon oils including, but not limited to, isoparaffins and olefins having greater than 20 carbon atoms; (iii) cosmetically-acceptable esters (as defined below); (iv) lanolin and derivatives thereof; (v) glyceryl esters of fatty acids or triglycerides, derived from animal or vegetable sources; (vi) fluorinated oils including, but not limited to, fluorinated silicones, fluorinated esters and perfluoropolyethers; and (vii) Guerbet esters formed by the reaction of a carboxylic acid with a Guerbet alcohol.

As used herein, "cosmetically-acceptable ester" refers to compounds formed by the reaction of a mono-, di- or tri-carboxylic acid with an aliphatic or aromatic alcohol that are not irritating or sensitizing when applied to the skin. The carboxylic acid may contain from 2 to 30 carbon atoms, and may be straight-chain or branched-chain, saturated or unsaturated. The carboxylic acid may also be substituted with one or more hydroxyl groups. The aliphatic or aromatic alcohol may contain 2 to 30 carbon atoms, may be straight-chain or branched-chain, saturated or unsaturated. The aliphatic or aromatic alcohol may contain one or more substituents including, for example, a hydroxyl group.

Among other things, the above-listed water-immiscible materials may provide emolliency. Other emollients known in the art may be used, including urethane emollients and conditioners sold under the tradename Polyderm by Alzo International, non-limiting examples of the latter including Polyderm PPI-CO-40 (PEG-40 Hydrogenated Castor Oil/IPDI Copolymer) and Polyderm PPI-SI (Dimethiconol/IPDI Copolymer).

By structuring agent is meant an ingredient that improves or increases the hardness of an oil as measured by test methods well-known to those of skill in the art including drop point and penetration.

One or more plasticizers may be added to compositions of the present invention to further modify spreadability and other application characteristics of the composition. Plasticizers may be present at concentrations of from about 0.01% to about 20%, preferably about 0.05% to about 15%, and more preferably from about 0.1% to about 10%.

Cold process emulsions according to the present invention may contain one or more surfactants at a concentration of from about 0.01% to about 20%, preferably from about 0.1% to about 15%, and more preferably from about 0.5% to about 10% by weight of the total composition. The surfactants may be amphoteric, anionic, cationic, or non-ionic.

Amphoteric surfactants suitable for use in compositions of the present invention include propionates, alkyldimethyl betaines, alkylamido betaines, sulfobetaines, imidazoline.

Anionic surfactants suitable for use in compositions of the present invention include fatty alcohol sulfates, alpha olefin sulfonates, sulfosuccinates, phosphate esters, carboxylates and sarcosinates.

Cationic surfactants suitable for use in compositions of the present invention include alkyl quaternaries, alylamido quaternaries, imidazoline quaternaries.

Nonionic ionic surfactants suitable for use in compositions of the present invention include alkanolamides, ethoxylated amides, esters, alkoxylated alcohols, alkoxylated triglycerides, alkylpolyglucosides, amine oxides, sorbitan esters and ethoxylates.

Surfactants may also be silicone surfactants including, but not limited, dimethicone copolyols, alkyl dimethicone copolyols, silicone quaternary compounds, silicone phosphate esters and silicone esters.

Encapsulates

The cold processing formulation aids of the present invention may contain other materials embedded therein. Encapsulation may be achieved by mixing other materials with the required components of the cold processing aid of the present invention as taught herein. In one example, the other material(s) are mixed with the cold processing aid of the present invention in a molten state, before it is atomized and cooled to create a solid wax particle. Non-limiting examples of materials that can be embedded inside the cold processing formulation aids of the present invention include, but are not limited to, pigments, preservatives, fillers, active ingredients (either hydrophilic or lipophilic), polymers, fragrance ingredients (e.g., essential oils and aroma-producing chemicals of natural or synthetic origin), and mixtures thereof.

Oil-in-Water Emulsions Containing High Molecular Weight Polysaccharides

In another embodiment, the CPFA described herein is used in oil-in-water emulsions that are stabilized with polysaccharides, especially xanthan, a poly(glucomannan), or both.

U.S. Pat. No. 6,831,107 discloses that high molecular weight polysaccharides stabilize oil-in-water emulsions (O/W), without increasing the low-shear viscosity of the emulsion, and allows lower levels of emulsifiers to be used.

However, this patent also discloses that use of anionic materials, e.g. anionic surfactants, in combination with high molecular weight polysaccharides is highly disfavored because, among other reasons, the ionic material impairs the ability of the polysaccharide to stabilize the emulsion. Applicants have surprisingly discovered that, despite the fact that the CPFAs of the present invention include polymers having ionic or ionizable groups, the CPFAs are useful in oil-in-water emulsions that are stabilized with high molecular weight polysaccharides. When a CPFA of the type described herein is used, high temperature is not required to form the emulsion, provided that sufficient shear energy is supplied.

For example the CPFA can be incorporated at low temperature to provide rheology modification when higher viscosity products are desired. Emulsions made with a CPFAs can be used as such in a personal care product, or they can be used to make articles, e.g. pads impregnated with such a product.

In preferred embodiments of this aspect of the invention, a CPFA, an emulsifier, and emulsion stabilizer (polysachamide) are blended to provide a dry product that can be dispersed in water and readily then made into emulsions at low temperature. In these embodiments, it can be useful to use both high HLB and low HLB emulsifiers and optionally to include materials such as milling aids. Products according to this embodiment can be made by dry blending xanthan and polyglucomannan, emulsifiers and the CPFA and consolidating the blend, e.g. by extrusion, desirably at a temperature, sufficient that one or more of the components (typically one or more of the emulsifiers are at least partly melted and can so coat and/or bind the powder components especially the polysaccharides), to form pellets and then milling the pellets to a desired particle size. While less preferable with respect to energy/heat consumption, the use of CPFAs to thicken an O/W emulsion as described in this embodiment may also be useful in conventional heated emulsion processes.

A typical composition for such a dry blend, in parts by weight, is as follows: xanthan (3 to 8% wt/wt); polyglucomannan (3 to % 8 wt/wt); olive wax 84 to 94% wt/wt. The ratio of xanthan to polyglucomannan can be between 1:2 to 2:1.

Surface Coatings/Protectants

In addition to personal care applications, where compositions of the present invention containing CPFAs are applied to mammalian hair or skin, compositions containing CPFAs of the present invention may be applied as a protectant, moisturizer, sealer, to household, industrial, hospital and commercial hard surfaces as well as to the exterior surfaces of automotive and marine vehicles, including tires and wheels, recreational sports equipment, woven and non-woven fabrics. Protectant, moisturizer and/or sealer formulations within the scope of the present invention may be applied for example, to rubber, vinyl, plastic, leather, fabric, carpeting.

As used in the present application, by "protectant" is meant a consumer or industrial product, preferably a spray, that coats the surface to minimize the degradation of the coated material due to environmental factors and provide a durable and shiny appearance. The protectant spray may, and in certain embodiments does contain, either or both of (i) a UV absorbing or reflecting/scattering compound known in the art and/or (ii) a cleansing agent (e.g., a surfactant). In embodiments directed to cleansing agents, positively charged "dirt particles" are entrained in the aqueous phase of an emulsion containing the CPFA of the present invention. Dirt is repelled from the surface while the wax within the emulsion attaches to the "uncharged", now clean surface.

CPFAs of the present invention may also be used in furniture restoration, i.e., to fill cracks.

Topical Hydro-Alcoholic Antiseptic

A topically-applied, hydro-alcoholic antiseptic product, meeting the criteria of the Tentative Final Monograph for OTC Healthcare Antiseptic Drug Products (Jun. 17, 1994), is illustrated below:

OTC Antiseptic Example 1
    Phase A—Distilled Water (24%); Ethanol (70%)
    Phase B—Cold Processing Aid of Present Invention (6%) (Sunflower Wax, Polyacrylate Crosspolymer-6, sold under the tradename CPW S-ZEN by Jeen International)

OTC Antiseptic Example 2
    Phase A—Distilled Water (26%); Ethanol (65%); Amino Methyl Propanediol (1.0%); Glycerin 99.7% USP (3.0%)
    Phase B—Cold Processing Aid of Present Invention (5%) (Sunflower Wax, Acrylates/$C_{10-30}$ Alkyl Acrylate Crosspolymer, sold under the tradename CPW-SUN21 by Jeen International)

The above OTC antiseptic product is prepared using a cold process formulation aid of the present invention by mixing at room temperature the ingredients of Phase A and Phase B separately, and then adding Phase B to Phase A. Consistent with the above Tentative Final OTC Monograph, the level of alcohol in this product may be adjusted to between 60 and 95%. Each of the above formulation are non-drying and leave a silky after feel.

Biomaterials

Cold process formulation aids of the present invention may be used in the manufacture of biocompatible materials, including, but not limited to, fillings, coatings, implants and "scaffolding" (i.e., to provide temporary support and stability for damaged tissue and/or to provide a substrate for growth of bone or tissue). The CPFA may include one or more crosslinked or photocurable (e.g., by ultraviolet light) functional groups. In one preferred embodiment, the CPFA biomaterial contains a polysaccharide backbone, for example, chitosan as disclosed in U.S. Pat. No. 7,914,819.

Ceramics and Concrete

Cold process formulation aids of the present invention may be incorporated into concrete and ceramics, thereby internally sealing the concrete or ceramic body composition with wax beads. For ceramics made by a dry grinding process, a substantially dry, ceramic raw batch (also known as a ceramic body composition) in a loose pulverant state (e.g., containing about 1% uncombined water with not more than 6% organic material) is admixed with a wax-water emulsion formed with one or more cold process formulation aids of the present invention. The slurry is screened and spray dried to create a flowable mass of small globules of wax-bonded ceramic. The resulting wax-bonded ceramic material is molded to form desired shapes that are then fired. Manufacturing methods based on admixing the cold process formulation aid of the present invention into the ceramic raw batch are advantageous because they allow for shaping of finished tiles, dinnerware or other ceramic articles without relying on the inherent plasticity of the ceramic body composition. Alternatively, cold process formulation aids of the present invention may be added to a ceramic raw batch slurry in a wet grinding process. The slurry is filtered, dried and fired.

Compositions for Decorative Application to a Surface

In other embodiments, the cold process formulation aid of the present invention ("CPFA") can be used in the manufacture of compositions, especially colored compositions, to be applied to decorate a surface, for example crayons, water colors, and water-based inks and paints.

In crayon embodiments, the CPFA may be at varying concentrations (e.g., 10%, 50%, or 75%) with a conventional crayon wax such as candle wax, and a pigment (typically 3% to 20%, by weight, of the total composition). The combination is heated until it melts into a homogeneous liquid (about 40° C.). The mixture is then heated to about 82° C. The liquid combination is poured into a preheated mold of crayon-shaped holes. Water (at about 13° C.) is used to cool the mold, forming crayons in from 3 to 9 minutes. Use of the CPFA of the present invention provides for improved dispersion of the pigment and smoother transfer of the crayon composition to the surface to be decorated.

The CPFA of the present invention is advantageously used in formulating gum-arabic based water color paints to provide an improved more stable dispersion of the dye or pigment, and an improved smoothness and texture when the water color is applied to the surface to be decorated. Use of the CPFA of the present invention allows the water color paint to be made at low temperature, especially at or about room temperature, allowing even heat sensitive dyes of pigments to be used in the water color.

As a non-limiting example, a water color paint is made by combining water, gum arabic, pigment, optionally glycerin and/or PEG, and CPFA (at 2% to 10% by weight) at a temperature not exceeding 35° C. When cooled to room temperature, the water color has a smooth, easy flowing texture, and can be applied with a minimum of drip or run. A typical base (vehicle) for water color formulation formulation is as follows: 80% water soluble, waxy polyethylene glycol, 4% stearyl alcohol, 6% polyhydric alcohol, 5% water by volume, and 5% by weight of CPFA. The base can be combined with the desired amount of pigment. The vehicle is particularly useful with cobalt violet, viridian or cadmium red that tend to separate from the vehicle.

In ink embodiments, the CPFA of the present invention is used as a flatting agent in conventional ink formulations to improve the surface properties of the known ink or paint formulations.

As a non-limiting example of a printing ink within the scope of the present invention, a CPFA may be added to the ink formulation in an amount of from about 3% to about 14%, based on the total weight of the formulation. Use of the CPFA of the present invention allows the ink to be formulated at relatively low temperature. Use of the CPFA of the present invention improves, among other things, bleed and rub-resistance of the ink.

In a water-based paint, the CPFA of the present invention may be used at about 1% to about 6%, based on the total weight of the paint. Inclusion of the CPFA of the present invention reduces gloss and improves the scratch and "black heel" resistance of the dry paint.

Internal sealing of concrete or ceramic tiles with cold processing formulating aids of the present invention is further illustrated by the following example. A portion of a wet (i.e., pourable) concrete mix is replaced with a cold process formulation aid of the present invention, in the form of a powder. The powder is mixed with other components of the concrete until it is well dispersed. The concrete is then cured. After the desired strength is achieved, the concrete is heated; this causes the powder to melt and flow into capillaries and pores of the concrete. By way of further example, a concrete bridge deck having a depth of three inches and conforming to standards promulgated by the Federal Highway Administration is made by replacing about 8% of a concrete mix with a cold processing aid of the present invention and heating the resulting mixture for approximately 5 to 9 hours.

Cold Process Emulsion Formed from Dual-Chambered Dispenser or Kit

A cold process formulation aid of the present invention, either in powder or paste, is stored in one side of dual-chambered container. On the other side of the container is separately stored an aqueous medium. The aqueous medium and cold process formulation aid are co-dispensed, forming an emulsion or hydrogel.

A cold process formulation aid of the present invention is admixed with an aqueous medium forming an aqueous base, which is then stored in one side of dual-chambered container. On the other side of the container is separately stored a combination of non-aqueous ingredients (e.g., an oil phase). The aqueous base and oil phase are co-dispensed, forming an emulsion or hydrogel.

A kit is provided to a user comprising (i) a cold process formulation aid of the present invention product in the form of a powder (e.g., in an sealed aluminum sachet) and (ii) an aqueous medium and/or (iii) an oil phase. The user is instructed to combine the powder with the aqueous medium or to combine distilled or tap water with the powder. The user is then further instructed to add the oil phase, thereby creating an emulsion of hydrogel.

Formulation Example 1

CPW-EW1 LP/CPW-2 Lotion (J2-56)

| A | DI Water | Distilled water | | 81.0 |
|---|---|---|---|---|
| A | Jeesperse ® CPW-EW1LP | Stearic Acid, Ceteareth-20, Cetyl Stearyl Alcohol, Sodium Polyacrylate | Jeen Int'l | 7.0 |
| A | Jeesperse ® CPW-2 | Polyethylene, Sodium Polyacrylate | Jeen Int'l | 2.0 |
| A | Triethanolamine 99% | Triethanolamine | Jeen Int'l | 1.0 |
| B | Mineral Oil | Mineral Oil | Carnation | 2.0 |
| B | Jeechem ® IPM | Isopropyl Myristate | Jeen Int'l | 2.0 |
| B | Jeesilc ® PDS-350 | Dimethicone | Jeen Int'l | 2.0 |
| B | Glycerine 99% | Glycerine | Jeen Int'l | 1.0 |
| B | Vitamin E USP | DL-Alpha Tocopheryl Acetate | Jeen Int'l | 0.4 |
| B | Creamy Peach Fragrance | Fragrance | Lenoci | 0.1 |
| B | Safflower Oil | *Carthamus Tinctorius* (Safflower) Seed Oil | Jeen Int'l | 0.5 |
| B | Jeecide ® G-II | Propylene Glycol, Diazolidinyl Urea, Methyl Paraben, Propyl Paraben | Jeen Int'l | 1.0 |

Add all ingredients from Phase A and mix until uniform. Add Phase B ingredients, one at the time and mix well until homogenous.

Formulation Example 2

CPW-EW-1 LP/CPW-2 Sunscreen (J2-60)

| A | DI Water | Distilled Water | | 66.7 |
|---|---|---|---|---|
| A | AMPD | Amino Methyl Propanediol | Angus | 0.7 |
| A | Jeesperse CPW-EW1 LP | Stearic Acid, Ceteareth-20, Cetearyl Alcohol, Sodium Polyacrylate | Jeen Int'l | 7.0 |
| A | Jeesperse ® CPW-2 | Polyethylene, Sodium Polyacrylate | Jeen Int'l | 2.0 |
| B | Glycerin 99.7% USP | Glycerin | Jeen Int'l | 2.0 |

| | | | | |
|---|---|---|---|---|
| B | Cherry Vanilla Fragrance | Fragrance | Lenoci | 0.1 |
| B | Vitamin E USP | Dl-Alpha Tocopheryl Acetate | Jeen Int'l | 0.5 |
| B | Jeecide ® G-II | Propylene Glycol, Diazolidinyl Urea, Methyl Paraben, Propyl Paraben | Jeen Int'l | 1.0 |
| C | Sunscreen Blend* | | Jeen Int'l | 20.0 |

Combine DI Water with AMPD and mix until uniform. Add Jeesperse's one at the time and mix until homogenous. Add phase B and C ingredients and mix until uniform.

*The following FDA-approved sunscreens and sunblocks may be used in sunscreen blend: p-Aminobenzoic acid up to 15%; Avobenzone up to 3%; Cinoxate up to 3%; Dioxybenzone up to 3%; Homosalate up to 15%; Menthyl anthranilate up to 5%; Octocrylene up to 10%; Octylmethoxycinnamate (Octinoxate) up to 7.5%; Octyl salicylate up to 5%; Oxybenzone up to 6%; Padimate 0 up to 8%; Phenylbenzimidazole sulfonic acid (Ensulizole) up to 4%; Sulisobenzone up to 10%; Titanium dioxide up to 25%; Trolamine salicylate up to 12%; Zinc oxide up to 25%. FDA regulations known to those of skill in the art further describe permitted ingredient combinations. Other sunscreens and sunblocks are approved in countries outside the US and are suitable for inclusion in compositions of the present invention.

Formulation Example 3

CPW-CG-T Tanning Lotion (J2-85 MC)

| | | | | |
|---|---|---|---|---|
| A | Deionized Water | Water | | 78.0 |
| A | Jeesperse CPW-CG-T | Cetyl Alcohol, Sodium Acrylate/Sodium Acryloyl Dimethyl Taurate Copolymer, Glyceryl Stearate, Caprylic/Capric Triglyceride | Jeen Int'l | 5.0 |
| B | Dihydroxyacetone | Dihydroxyacetone | EMD Chemical | 3.0 |
| B | Coconut Oil | Cocos Nucifera (Coconut) Oil | Jeen Int'l | 2.0 |
| B | Jeesorb L-20NF | Polysorbate 20 | Jeen Int'l | 1.0 |
| B | Jeechem IPM | Isopropyl Myristate | Jeen Int'l | 5.0 |
| B | Jeechem ® BUGL | Butylene Glycol | Jeen Int'l | 2.0 |
| B | Jeesilc ® 35C | Dimethicone, Dimethicone Crosspolymer-3 | Jeen Int'l | 3.0 |
| B | Jeecide ® GII | Propylene Glycol, Diazolidinyl Urea, Methyl Paraben, Propyl Paraben | Jeen Int'l | 1.0 |

Mix Phase A at room temperature. Add Phase B and mix until homogenous.

Formulation Example 4

CPW-GCS Body Lotion (J7/51 A& B)

| | | | | | |
|---|---|---|---|---|---|
| A | DI Water | Distilled Water | | 72.30 | 77.30 |
| A | Glycerin 99 | Glycerin | Jeen Int'l | 4.00 | 4.00 |
| A | TEA 99 | Triethanolamine | Jeen Int'l | 0.70 | 0.70 |
| B | Jeesperse ® CPW-GCS | Stearic Acid, Cetearyl Alcohol, Glyceryl Stearate, PEG-100 Stearate, Sodium Polyacrylate | Jeen Int'l | 8.00 | 8.00 |
| C | Mineral Oil | Mineral Oil | Carnation | 8.00 | 5.00 |
| C | Jeesilc ® PDS-100 | Dimethicone | Jeen Int'l | 4.00 | 2.00 |
| D | Jeecide ® G II | Diazolidinyl Urea & Methylparaben & Propylparaben & Propylene Glycol | Jeen Int'l | 1.00 | 1.00 |
| D | Fragrance | Fragrance | | 2.00 | 2.00 |

Add D.I. Water, glycerin and the TEA. Mix until uniform using low speed homogenizing agitation. Sprinkle in Phase B ingredient and mix until the batch is smooth. Add Phase C ingredients one at a time to the batch and mix well using slow speed homogenization. Ad Phase D ingredients one at a time and mix with low speed homogenizing agitation.

Formulation Example 5

CPW-2+Jeesilc® 6056 (J8-23A)

| | | | | |
|---|---|---|---|---|
| A | Jeesperse ® CPW-2 | Polyethylene, Sodium Polyacrylate | Jeen Int'l | 5.00 |
| A | DI Water | Distilled Water | | 89.0 |
| A | Jeecide ® CAP-5 | Phenoxyethanol, Caprylyl Glycol, Potassium Sorbate, Water, Hexylene Glycol | Jeen Int'l | 1.00 |
| B | Jeesilc ® 6056 | Dimethicone, Dimethiconol, Laureth-4, Laureth-23 | Jeen Int'l | 5.00 |

Combine Phase A. Combine Phase B. Combine Phase A and Phase B and mix until homogenous.

Formulation Example 6

CPW-S Hydrogel Paint (J8-46)

| | | | | |
|---|---|---|---|---|
| A | Water | Water | | 60.6 |
| A | Shea Butter | Shea (Butyrospermum Parkii) Butter | Jeen Int'l | 5.00 |
| A | Cocoa Butter USP Deodorized | Theobroma Cacao (Cocoa) Seed Butter | Jeen Int'l | 2.00 |
| A | Coconut Oil | Cocos Nucifera (Coconut) Oil | Jeen Int'l | 5.00 |
| A | Jeechem ® CTG | Caprylic/Capric Triglyceride | Jeen Int'l | 5.00 |
| A | Jeecide ® CAP-5 | Phenoxyethanol, Caprylyl Glycol, Potassium Sorbate, Water, Hexylene Glycol | Jeen Int'l | 0.80 |
| A | Jeesilc ® EM-90 | Cetyl Peg/Ppg-10 Dimethicone | Jeen Int'l | 2.00 |
| A | Performa V 825 | Synthetic Wax | Presperse | 2.50 |
| B | Jeesperse ® CPW-S | Sunflower Wax, Sodium Polyacrylate | Jeen Int'l | 4.00 |
| C | SW40R7C | Red 7 | Kobo | 6.50 |
| C | SW60ER | Red Oxide | Kobo | 0.80 |
| C | SW55EB | Black Oxide | Kobo | 0.20 |
| C | Mica | Mica | Kobo | 2.60 |
| C | KTZ Ultrashimmer | Mica And $TiO_2$ | Kobo | 3.00 |

Mix and heat Phase A to 70-75'C. Add Phase B mix until homogenous. Add Phase C mix until homogenous. Mix while cooking to room temperature.

Formulation Example 7

CPW Hydrogen Peroxide (J8-62/62A)

| A | Hydrogen Peroxide | Hydrogen Peroxide (3% Solution) | | 90 | 90 |
|---|---|---|---|---|---|
| B | Jeesperse CPW-3 | Polyethylene, Sodium Polyacrylate | Jeen Int'l | 0 | 10 |

Add Phase B to Phase A while mixing. Mix until homogenous.

Formulation Example 8

CPW-S Hydrogel Paint (J9-67)

| A | Water | Water | | 59.3 |
|---|---|---|---|---|
| A | Shea Butter | Shea (*Butyrospermum Parkii*) Butter | Jeen Int'l | 5.00 |
| A | Cocoa Butter USP Deodorized | *Theobroma Cacao* (Cocoa) Seed Butter | Jeen Int' | 2.00 |
| A | Coconut Oil | *Cocos Nucifera* | Jeen Intl | 5.00 |
| A | Coconut Oil | *Cocos Nucifera* (Coconut) Oil | Jeen Intl | 5.00 |
| A | Jeechem ® CTG | Caprylic/Capric Triglyceride | Jeen Int'l | 5.00 |
| A | Jeecide ® CAP-5 | Phenoxyethanol, Caprylyl Glycol, Potassium Sorbate, Water, Hexylene Glycol | Jeen Int'l | 0.80 |
| A | Jeesilc ® EM-90 | Cetyl Peg/Ppg-10 Dimethicone | Jeen Int'l | 2.00 |
| A | Performa V 825 | Synthetic Wax | Presperse | 2.50 |
| B | Jeesperse ® CPW-S | Sunflower Wax, Sodium Polyacrylate | Jeen Int'l | 4.00 |
| C | SW40R7C | Red 7 | Kobo | 1.00 |
| C | SW60ER | Red Oxide | Kobo | 5.00 |
| C | SW55EB | Black Oxide | Kobo | 1.40 |
| C | Mica | Mica | Kobo | 3.00 |
| C | KTZ Copper | Mica And Iron Oxide | Kobo | 3.00 |
| C | Superb Silver | Mica And Titanium | Kobo | 1.00 |

Mix and heat Phase A to 70-75'C. Add Phase B mix until homogenous. Add Phase C mix until homogenous. Mix while cooking to room temperature.

Formulation Example 9

CPW-DG ST1 (J8-79)

| A | Water | Water | | 70.0 |
|---|---|---|---|---|
| A | Jeesperse ® CPW-DG ST1 | Titanium Dioxide, Polyethylene, Caprylic/Capric Triglyceride, Sodium Polyacrylate, Yellow Iron Oxide, Red Iron Oxide, Black Iron Oxide | Jeen Int'l | 18.0 |
| B | Jeechem ® ISNP | Isostearyl Neopentanoate | Jeen Int'l | 4.00 |
| B | Jeesilc ® PDS 5 | Dimethicone | Jeen Int'l | 3.50 |
| B | Jeecide ® CAP-5 | Phenoxyethanol, Caprylyl Glycol, Potassium Sorbate, Water, Hexylene Glycol | Jeen Int'l | 1.00 |
| C | Mica | Mica | Kobo | 2.6 |
| C | BPD-500 | Trimethyl Hexylactone Crosspolymer (and) Silica | Kobo | 0.90 |

Mix Phase A. Mix Phase B until homogenous. Add Phase B to Phase A mix until homogenous. Add Phase C mix until homogenous.

Formulation Example 10

CPW-S Mascara J8-87/J8-88 CPW-S J8-87 Base

| A | Water | Water | | 89.0 |
|---|---|---|---|---|
| A | Jeesperse ® CPW-S | *Helianthuss Annuus* (Sunflower) Seed Wax, Sodium Polyacrylate | Jeen Int'l | 10.0 |
| B | Jeecide ® CAP-5 | Phenoxyethanol, Caprylyl Glycol, Potassium Sorbate, Water, Hexylene Glycol | Jeen Int'l | 1.00 |

Mix Phase A until homogenous. Add in Phase B and mix.

Formulation Example 11

CPW-S Mascara (J8-87 and J8-88)

| A | Jeesperse ® CPW-S J8-87 Base | Water, Jeesperse CPW-S Jeecide ® CAP-5 | Jeen Int'l | 60.3 | 71.1 |
|---|---|---|---|---|---|
| B | LUVISET PUR | Water, Polyurethane, Ethanol | BASF | 30.7 | — |
| B | FA 4002 ID | Isododecane, Silicone Acrylate | Dow Corning | — | 17.4 |
| B | Jeesilc ® EM-90 | Cetyl PEG/PPG-10 Dimethicone | Jeen Int'l | — | 1.00 |
| C | Black Oxide 11J2 | Iron Oxide (77499), Triethoxycaprylyl Silane | Kobo | 9.00 | 10.5 |

Mix Phase A until homogenous. Add in Phase B and mix. Add in Phase C and mix.

Formulation Example 12

CPW-3 Velvet Primer (J9-52A NJM)

| A | DI Water | Distilled water | | 75.0 |
|---|---|---|---|---|
| A | Jeesperse ® CPW-3 | Polyethylene, Sodium Polyacrylate | Jeen Int'l | 6.0 |
| B | Jeelux ® D2T | Isohexadecane, Dimethicone, Triisosteryl Citrate, Bis-Vinyl Dimethicone/Dimethicone Copolymer | Jeen Int'l | 5.0 |
| B | Jeesilc ® EM-90 | Cetyl PEG/PPG-10 Dimethicone | Jeen Int'l | 2.0 |
| B | Jeesilc ® DS-8 | PEG-8 Dimethicone | Jeen Int'l | 1.0 |
| B | Jeechem ® CTG | Caprylic/Capric Triglyceride | Jeen Int'l | 10.0 |

-continued

| | | | | |
|---|---|---|---|---|
| B | Jeecide ® CAP-5 | Phenoxyethanol, Caprylyl Glycol, Potassium Sorbate, Water, Hexylene Glycol | Jeen Int'l | 1.0 |

Mix Phase A to room temperature. Add Phase B until homogenous

Formulation Example 13

CPW-EW1LP Cool Cream (J9-72)

| | | | | |
|---|---|---|---|---|
| A | DI Water | Distilled water | | 78.0 |
| A | Jeesperse ® CPW-EW1LP | Stearic Acid, Ceteareth-20, Cetyl Stearyl Alcohol, Sodium Polyacrylate | Jeen Int'l | 10.0 |
| A | Triethanolamine 99% | Triethanolamine | Jeen Int'l | 1.0 |
| B | Jeechem ® IPM | Isopropyl Myristate | Jeen Int'l | 2.0 |
| B | Jeesilc ® PDS-350 | Dimethicone | Jeen Int'l | 3.0 |
| B | Glycerine 99% | Glycerine | Jeen Int'l | 3.0 |
| B | Sesame Oil | *Sesamum Indicum* Seed Oil | Jeen Int'l | 2.0 |
| B | Jeecide ® G-II | Propylene Glycol, Diazolidinyl Urea, Methyl Paraben, Propyl Paraben | Jeen Int'l | 1.0 |

Mix Phase A to room temperature. Add Phase B until homogenous

| | | | | |
|---|---|---|---|---|
| A | DI Water | Distilled water | | 69.1 |
| A | Jeesperse ® CPW-EW1LP | Stearic Acid, Ceteareth-20, Cetyl Stearyl Alcohol, Sodium Polyacrylate | Jeen Int'l | 9.0 |
| A | Triethanolamine 99% | Triethanolamine | Jeen Int'l | 0.9 |
| B | Jeecide ® G-II | Propylene Glycol, Diazolidinyl Urea, Methyl Paraben, Propyl Paraben | Jeen Int'l | 1.0 |
| B | Sunscreen Blend | | Jeen Int'l | 20.0 |

Formulation Example 14

CPW-EW1LP Sunscreen (J9-74NJM)

Mix Phase A to room temperature. Add Phase B until homogenous.

Formulation Example 15

CPW-B Cool Lotion (J9-76B-NJM)

| | | | | |
|---|---|---|---|---|
| A | DI Water | Distilled water | | 76.0 |
| A | Jeesperse ® CPW-B | Beeswax, Sodium Polyacrylate | Jeen Int'l | 7.0 |
| B | Mineral Oil | Mineral Oil | Carnation | 4.0 |
| B | Jeechem ® IPM | Isopropyl Myristate | Jeen Int'l | 2.0 |
| B | Jeesilc ® PDS-350 | Dimethicone | Jeen Int'l | 3.0 |
| B | Glycerine 99% | Glycerine | Jeen Int'l | 5.0 |
| B | Sweet Almond Oil | *Prunus Amygdalus Dulcis* (Sweet Almond) Oil | Jeen Int'l | 1.0 |

-continued

| | | | | |
|---|---|---|---|---|
| B | Avocado Oil | *Persea Gratissima* (Avocado) Oil | | 1.0 |
| B | Jeecide ® G-II | Propylene Glycol, Diazolidinyl Urea, Methyl Paraben, Propyl Paraben | Jeen Int'l | 1.0 |

Mix Phase A to room temperature. Add Phase B until homogenous.

Formulation Example 16

CPW-BC Cool Cream (J9-77 NJM)

| | | | | |
|---|---|---|---|---|
| A | DI Water | Distilled Water | | 76.0 |
| A | Jeesperse CPW-BC | *Theobroma Cacao* (Cocoa) Seed Butter, Beeswax, Yellow Refined, Sodium Polyacrylate | Jeen Int'l | 10.0 |
| B | Mineral Oil | Mineral Oil | Jeen Int'l | 4.0 |
| B | Sweet Almond Oil | *Prunus Amygdalus Dulcis* (Sweet Almond) Oil | Jeen Int'l | 1.0 |
| B | Jeesilc ® PDS-350 | Dimethicone | Jeen Int'l | 3.0 |
| B | Glycerine 99% | Glycerine | Jeen Int'l | 2.0 |
| B | Avocado Oil | *Persea Gratissima* (Avocado) Oil | Jeen Int'l | 1.0 |
| B | Jeechem ® IPM, NF | Isopropyl Myristate | Jeen Int'l | 2.0 |
| B | Jeecide ® G-II | Propylene Glycol, Diazolidinyl Urea, Methyl Paraben, Propyl Paraben | Jeen Int'l | 1.0 |

Mix Phase A at room temperature. Add Phase B until homogenous.

Formulation Example 17

CPW-BC Cool Cream (J9-78 NJM)

| | | | | |
|---|---|---|---|---|
| A | DI Water | Distilled Water | | 74.0 |
| A | Jeesperse CPW-BC | *Theobroma Cacao* (Cocoa) Seed Butter, Beeswax, Yellow Refined, Sodium Polyacrylate | Jeen Int'l | 10.0 |
| B | Mineral Oil | Mineral Oil | Jeen Int'l | 4.0 |
| B | Sweet Almond Oil | *Prunus Amygdalus Dulcis* (Sweet Almond) Oil | Jeen Int'l | 1.0 |
| B | Jeesilc ® PDS-350 | Dimethicone | Jeen Int'l | 3.0 |
| B | Glycerine 99% | Glycerine | Jeen Int'l | 2.0 |
| B | Avocado Oil | *Persea Gratissima* (Avocado) Oil | Jeen Int'l | 1.0 |
| B | Jeechem ® IPM, NF | Isopropyl Myristate | Jeen Int'l | 2.0 |
| B | BP-Biopeptide SC | Saccharomyces/Selenium Ferment | Botanicals Plus | 1.0 |
| B | BP-Glucan MC | Beta Glucan | Botanicals Plus | 1.0 |
| B | Jeecide ® G-II | Propylene Glycol, Diazolidinyl Urea, Methyl Paraben, Propyl Paraben | Jeen Int'l | 1.0 |

Mix Phase A at room temperature. Add Phase B until homogenous.

Formulation Example 18

CPW-P Cool Lotion (J9-79 NJM)

| | | | | |
|---|---|---|---|---|
| A | DI Water | Distilled Water | | 82.0 |
| A | Jeesperse ® CPW-P | Cetearyl Alcohol, Sodium Polyacrylate, Stearateh-20, Polysorbate 60 | Jeen Int'l | 5.0 |
| B | Sesame Oil | *Sesamum Indicum* (Sesame) Seed Oil | Jeen Int'l | 2.0 |
| B | Jeesilc ® PDS-350 | Dimethicone | Jeen Int'l | 2.5 |
| B | Glycerine 99% | Glycerine | Jeen Int'l | 3.5 |
| B | Jeechem ® IPM, NF | Isopropyl Myristate | Jeen Int'l | 2.0 |
| B | BP-Biopeptide SC | Saccharomyces/Selenium Ferment | Botanicals Plus | 1.0 |
| B | BP-Glucan MC | Beta Glucan | Botanicals Plus | 1.0 |
| B | Jeecide ® G-II | Propylene Glycol, Diazolidinyl Urea, Methyl Paraben, Propyl Paraben | Jeen Int'l | 1.0 |

Mix Phase A at room temperature. Add Phase B until homogenous.

Formulation Example 19

CPW-3 Sunscreen (J9-80B NJM)

| | | | | |
|---|---|---|---|---|
| A | DI Water | Distilled water | | 69.0 |
| A | Jeesperse ® CPW-3 | Polyethylene, Sodium Polyacrylate | Jeen Int'l | 9.0 |
| A | Jeesilc ® EM-90 | Cetyl PEG/PPG-10 Dimethicone | Jeen Int'l | 1.0 |
| B | Jeecide ® G-II | Propylene Glycol, Diazolidinyl Urea, Methyl Paraben, Propyl Paraben | Jeen Int'l | 1.0 |
| B | Sunscreen Blend | Avobenzone (9.2%), Homosalate (46.6%), Octisalate (17.5%), Octocrylene (8.6%) Oxybenzone (18.1%) | Jeen Int'l | 20.0 |

Mix Phase A at room temperature. Add Phase B until homogenous.

Formulation Example 20

CPW5-PVPK-30 Lifting Skin Renewal (J9-84B)

| | | | | |
|---|---|---|---|---|
| A | DI Water | Distilled water | | 88.0 |
| A | Jeesperse ® CPW5-PVPK-30 | Polyethylene, Polyvinylpyrrolidone, Sodium Polyacrylate | Jeen Int'l | 10.0 |
| B | Jeecide ® G-II | Propylene Glycol, Diazolidinyl Urea, Methyl Paraben, Propyl Paraben | | 1.0 |
| B | Jeesilc ® PDS-1 | Dimethicone | Jeen Int'l | 1.0 |

Mix Phase A. Mix Phase B until homogenous. Add Phase B to Phase A mix until homogenous.

Formulation Example 21

CPW-BC Natural Hydrogel Cream (J9-90 NJM)

| | | | | |
|---|---|---|---|---|
| A | DI Water | Distilled water | | 76.0 |
| A | Jeesperse ® CPW-BC | *Theobroma Cacao* (Cocoa) Seed Butter, Beeswax, Yellow Refined, Sodium Polyacrylate | Jeen Int'l | 10.0 |
| A | Coconut Oil | *Cocos Nucifera* Oil | Jeen Int'l | 3.0 |
| A | Shea Butter | *Butyrospermum Parkii* Butter | Jeen Int'l | 5.0 |
| B | Jeechem ® CTG | Caprylic/Capric Triglyceride | Jeen Int'l | 5.0 |
| B | Jeecide ® CAP-5 | Phenoxyethanol, Caprylyl Glycol, Potassium Sorbate, Water, Hexylene Glycol | Jeen Int'l | 1.0 |

Mix Phase A at room temperature. Add Phase B until homogenous.

Formulation Example 22

CPW-EW1LP 110 Lotion (J10-11D)

| | | | | |
|---|---|---|---|---|
| A | DI Water | Distilled water | | 78.0 |
| A | Triethanolamine 99% | Triethanolamine | Jeen Int'l | 1.0 |
| A | Jeesperse ® CPW-EW1LP | Stearic Acid, Ceteareth-20, Cetyl Stearyl Alcohol, Sodium Polyacrylate | Jeen Int'l | 10.0 |
| B | Jeechem ® IPM | Isopropyl Myristate | Jeen Int'l | 2.0 |
| B | Glycerine 99% | Glycerine | Jeen Int'l | 3.0 |
| B | Sesame Oil | *Sesamum Indicum* Seed Oil | Jeen Int'l | 2.0 |
| B | Jeesilc ® 110 | Dimethicone | Jeen Int'l | 2.0 |
| B | Baby Powder Scent | Fragrance | | 1.0 |
| B | Jeecide ® G-II | Propylene Glycol, Diazolidinyl Urea, Methyl Paraben, Propyl Paraben | Jeen Int'l | 1.0 |

Mix Phase A. Add Phase B until homogenous. Add Phase C and mix.

Formulation Example 23

CPW-2 110 Lotion (J10-12B)

| | | | | |
|---|---|---|---|---|
| A | DI Water | Distilled water | | 80.0 |
| A | Jeesperse ® CPW-2 | Polyethylene, Sodium Polyacrylate | Jeen Int'l | 10.0 |
| B | Jeechem ® IPM | Isopropyl Myristate | Jeen Int'l | 2.0 |
| B | Glycerine 99% | Glycerine | Jeen Int'l | 3.0 |
| B | Sesame Oil | *Sesamum Indicum* Seed Oil | Jeen Int'l | 2.0 |
| B | Jeesilc ® ® 110 | Dimethicone | Jeen Int'l | 2.0 |
| B | Jeecide ® G-II | Propylene Glycol, Diazolidinyl Urea, Methyl Paraben, Propyl Paraben | Jeen Int'l | 1.0 |

Mix Phase A to room temperature. Add Phase B until homogenous.

Formulation Example 24

LV-CPW Spray Lotion (J10-45 JM)

| | | | | |
|---|---|---|---|---|
| A | Deionized Water | Water | | 90.0 |
| A | Jeesperse CPW-CG-T | Cetyl Alcohol, Sodium Acrylate/Sodium Acryloyl Dimethyl Taurate Copolymer, Glyceryl Stearate | Jeen Int'l | 1.5 |
| A | Jeechem ® ISP | Isostearyl Palmitate & Triisostearyl Citrate | Jeen Int'l | 2.0 |
| A | Jeesperse CPW-S | *Helianthus Annuus* (Sunflower) Seed Wax, 2-Propenoic Acid, Homopolymer | Jeen Int'l | 0.5 |
| B | Jeesilc ® DMC-153 | Dimethicone, Dimethiconol | Jeen Int'l | 3.0 |
| B | Jeesorb L-20 | Polysorbate 20 | Jeen Int'l | 1.9 |
| B | Jeecide ® GII | Propylene Glycol, Diazolidinyl Urea, Methyl Paraben, Propyl Paraben | Jeen Int'l | 0.8 |

Mix Phase A at room temperature. Add Phase B until homogenous.

Formulation Example 25

HV-CPW Spray Lotion (J10-45A JM)

| | | | | |
|---|---|---|---|---|
| A | Deionized Water | Water | | 90.0 |
| A | Jeesperse | Cetyl Alcohol, Sodium | | |
| A | Jeesperse CPW-CG-T | Cetyl Alcohol, Sodium Acrylate/Sodium Acryloyl Dimethyl Taurate Copolymer, Glyceryl Stearate | Jeen Int'l | 2.0 |
| A | Jeechem ® ISP | Isostearyl Palmitate & Triisostearyl Citrate | Jeen Int'l | 2.0 |
| A | Jeesperse CPW-S | *Helianthus Annuus* (Sunflower) Seed Wax, 2-Propenoic Acid, Homopolymer | Jeen Int'l | 0.5 |
| B | Jeesilc ® DMC-153 | Dimethicone, Dimethiconol | Jeen Int'l | 3.0 |
| B | Jeesorb ® STS-20 | Polysorbate 65 | Jeen Int'l | 1.7 |
| B | Jeecide ® GII | Propylene Glycol, Diazolidinyl Urea, Methyl Paraben, Propyl Paraben | Jeen Int'l | 0.8 |

Mix Phase A at room temperature. Add Phase B until homogenous.

Formulation Example 26

LV-CPW Spray Lotion (J10-45B JM)

| | | | | |
|---|---|---|---|---|
| A | Deionized Water | Water | | 90.0 |
| A | Jeesperse ® CPW-CG-T | Cetyl Alcohol, Sodium Acrylate/Sodium Acryloyl Dimethyl Taurate Copolymer, Glyceryl Stearate | Jeen Int'l | 1.5 |
| A | Jeechem ® ISP | Isostearyl Palmitate & Triisostearyl Citrate | Jeen Int'l | 2.0 |
| A | Jeesperse CPW-S | *Helianthus Annuus* (Sunflower) Seed Wax, 2-Propenoic Acid, Homopolymer | Jeen Int'l | 0.4 |
| B | Jeesilc ® DMC-153 | Dimethicone, Dimethiconol | Jeen Int'l | 3.0 |
| B | Jeesorb ® STS-20 | Polysorbate 65 | Jeen Int'l | 2.0 |
| B | Jeecide ® GII | Propylene Glycol, Diazolidinyl Urea, Methyl Paraben, Propyl Paraben | Jeen Int'l | 0.8 |

Mix Phase A at room temperature. Add Phase B until homogenous.

Formulation Example 27

CPW-5 Cream (J11-2 NJM)

| | | | | |
|---|---|---|---|---|
| A | DI Water | Distilled Water | | 80.5 |
| A | Jeesperse ® CPW-5 | Polyethylene, Sodium Polyacrylate | Jeen Int'l | 5.0 |
| B | Coconut Oil | *Cocos Nucifera* (Coconut) Oil | Jeen Int'l | 3.0 |
| B | Avocado Oil | *Persea Gratissima* (Avocado) Oil | Jeen Int'l | 3.0 |
| B | Jeesilc ® PDS-350 | Dimethicone | Jeen Int'l | 2.0 |
| B | Glycerine 99% | Glycerine | | 3.5 |
| B | Jeechem ® IPM, NF | Isopropyl Myristate | Jeen Int'l | 2.0 |
| B | Jeecide ® G-II | Propylene Glycol, Diazolidinyl Urea, Methyl Paraben, Propyl Paraben | Jeen Int'l | 1.0 |

Mix Phase A at room temperature. Add Phase B until homogenous.

Formulation Example 28

CPW-BC Eye Shadow (J11-37)

| | | | | |
|---|---|---|---|---|
| A | DI Water | Distilled water | | 68.0 |
| A | Jeesperse ® CPW-BC | *Theobroma Cacao* (Cocoa) Seed Butter, Yellow Beeswax, Sodium Polyacyrlate | Jeen Int'l | 6.50 |
| A | PVPK-30 | Polvinylpyrrolidone | ISP | 3.50 |
| A | BTD 11S2 | Titanium Dioxide (AND) Triethoxycaprylylsilane | Kobo | 4.00 |
| B | Jeecide ® G-II | Propylene Glycol, Diazolidinyl Urea, Methyl Paraben, Propyl Paraben | Jeen Int'l | 0.50 |
| B | Jeesilc ® PDS-1 | Dimethicone | Jeen Int'l | 4.00 |
| B | Mica | Mica | Kobo | 4.00 |
| B | Interfine Green | Mica and Titanium Dioxide | Kobo | 7.50 |
| B | El Dorado Bronze MMM.500 | Bronze Oxide | Impact Color | 2.00 |

Mix Phase A at room temperature. Add Phase B and homogenize.

Formulation Example 29

CPW-S Sunscreen (J11-53 NJM)

| | | | | |
|---|---|---|---|---|
| A | DI Water | Distilled Water | | 68.0 |
| A | Jeesperse ® CPW-S | Sunflower Wax, Sodium Polyacrylate | Jeen Int'l | 10.0 |
| A | Jeesilc ® EM-90 | Cetyl Peg/Ppg-10 Dimethicone | Jeen Int'l | 1.0 |
| B | Jeecide ® G-II | Propylene Glycol, Diazolidinyl Urea, Methyl Paraben, Propyl Paraben | Jeen Int'l | 1.0 |
| B | Sunscreen Blend | | Jeen Int'l | 20.0 |

Mix Phase A to room temperature. Add Phase B until homogenous.

Formulation Example 30

CPW-BC Eye Shadow (J11-83 NJM)

| | | | | |
|---|---|---|---|---|
| A | DI Water | Distilled Water | | 66.5 |
| A | Jeesperse CPW-BC | *Theobroma Cacao* (Cocoa) Seed Butter, Beeswax, Yellow Refined, Sodium Polyacrylate | Jeen Int'l | 3.0 |
| A | Jeesilc ® DMBF Aqua Base | Dimethicone (and) Cetyl PEG/PPG-10 Dimethicone (and) Bis-Vinyl Dimethicone/Dimethicone Copolymer | Jeen Int'l | 7.0 |
| A | Jeesilc ® PDS.1 | Dimethicone | Jeen Int'l | 4.0 |
| A | Mineral Oil | Mineral Oil | Jeen Int'l | 0.5 |
| A | PVPK-30 | Polyvinylpyrrolidone | ISP | 4.0 |
| A | BTD 11S2 | Titanium Dioxide (and) Triethoxycaprylylsilane | Kobo | 2.0 |
| A | Jeecide ® GII | Propylene Glycol, Diazolidinyl Urea, Methyl Paraben, Propyl Paraben | Jeen Int'l | 1.0 |
| B | KobomicaL-25 | Mica | Kobo | 3.0 |
| B | KTZ Shimmer Green | Mica And Titanium Dioxide | Kobo | 5.0 |
| B | Bichroma Magenta | Bismuth Oxychloride And Mica And Carmine | Impact Color | 2.0 |
| B | Diamond Red Rose | Mica And Titanium Dioxide And Carmine And Tin Oxide And Methicone | Impact Color | 1.0 |
| B | Jeesilc ® DMC 19-3 | Peg-12 Dimethicone | Jeen Int'l | 1.0 |

Mix Phase A until homogenous. Add in Phase B and mix.

Formulation Example 31

CPW-CG-T Creamy Sunscreen (J11-84 NJM)

| | | | | |
|---|---|---|---|---|
| A | DI Water | Distilled Water | | 56.0 |
| A | Jeesperse CPW-CGT | Cetyl Alcohol, Sodium Acrylate/Sodium Acryloyl Dimethyl Taurate Copolymer, Glyceryl Stearate | Jeen Int'l | 4.0 |
| A | Jeesilc ® DMBF | Dimethicone, Bis-Vinyl Dimethicone/Dimethicone Copolymer | Jeen Int'l | 9.0 |
| B | Jeesperse T50TN | C12-15 Alkyl Benzoate, Titanium Dioxide, Triethoxycaprylylsilane, Castor Oil Phosphate | Jeen Int'l | 17.0 |
| B | Jeeesperse ZO-65OP | Zinc Oxide USP (and)Dimethicone(and) Octyl Palmitate | Jeen Int'l | 7.0 |
| B | Jeesilc ® 3D-5 | Dimethicone Crosspolymer-3, Cyclomethicone | Jeen Int'l | 2.0 |
| B | Jeesilc ® DMC-153 | Dimethicone, Dimethiconol | Jeen Int'l | 4.0 |
| B | Jeecide ® G-II | Propylene Glycol, Diazolidinyl Urea, Methyl Paraben, Propyl Paraben | Jeen Int'l | 1.0 |

Add all ingredients from Phase A and mix until uniform. Add Phase B ingredients, one at the time and mix well until homogenous

Formulation Example 32

CPW-Sun21 Anti-Bacterial (J11-88B NJM)

| | | | | |
|---|---|---|---|---|
| A | DI Water | Distilled water | | 30 |
| A | SDA 40 | Ethanol | | 63 |
| A | AMPD | Amino Methyl Propanediol | Angus | 0.5 |
| B | Glycerin 99.7% USP | Glycerin | Jeen Int'l | 3.0 |
| B | Jeesperse CPW-SUN21 | *Helianthux Annuus* (Sunflower) Seed Wax and Acrylates/C10-30 Alkyl Crosspolymer | Jeen Int'l | 3.5 |

Mix Phase A to room temperature. Add Phase B until homogenous.

Formulation Example 33

CPW-S Natural Hydrogel (11-38NJM)

| | | | | |
|---|---|---|---|---|
| A | DI Water | Water | | 76.0 |
| A | Jeesperse ® CPW-S | Sunflower Wax, Sodium Polyacrylate | Jeen Int'l | 6.00 |
| A | Shea Butter | Shea (*Butyrospermum Parkii*) Butter | Jeen Int'l | 5.00 |
| A | Safflower Oil | *Carthamus Tinctorius* (Safflower) Seed Oil | Jeen Int'l | 2.00 |
| A | Coconut Oil | *Cocos Nucifera* (Coconut) OIL | Jeen Intl | 5.00 |
| A | Jeechem ® CTG | Caprylic/Capric Triglyceride | Jeen Int'l | 5.00 |
| B | Jeecide ® CAP-5 | Phenoxyethanol, Caprylyl Glycol, Potassium Sorbate, Water, Hexylene Glycol | Jeen Int'l | 1.00 |

Mix Phase A at room temperature. Add Phase B and mix until homogenous.

Formulation Example 34

CPW-CG-T Moisture Lotion (J11-92 NJM)

| | | | | |
|---|---|---|---|---|
| A | Deionized Water | Water | | 83.0 |
| A | Jeesperse ® CPW-CGT | Cetyl Alcohol, Sodium Acrylate/Sodium Acryloyl Dimethyl Taurate | Jeen Int'l | 5.0 |

-continued

| | | | | |
|---|---|---|---|---|
| A | Glycerin | Copolymer, Glyceryl Stearate, Caprylic/Capric Triglyceride Glycerin | Jeen Int'l | 5.0 |
| A | Jeesilc ® PDS 350 | Dimethicone | Jeen Int'l | 2.0 |
| B | Jeesilc ® 110 | Dimethicone | Jeen Int'l | 4.5 |
| B | Jeecide ® GII | Propylene Glycol, Diazolidinyl Urea, Methyl Paraben, Propyl Paraben | Jeen Int'l | 0.5 |

Mix Phase A at room temperature. Add Phase B until homogenous

Formulation Example 35

CPW-CG-T Eye Shadow (J11-95 NJM)

| | | | | |
|---|---|---|---|---|
| A | DI Water | Distilled Water | | 68.5 |
| A | Jeesperse ® CPW-CG-T | Cetyl Alcohol, Sodium Acrylate/Sodium Acryloyl | Jeen Int'l | 3.0 |
| A | Jeesperse ® CPW-CG-T | Cetyl Alcohol, Sodium Acrylate/Sodium Acryloyl Dimethyl Taurate Copolymer, Glyceryl Stearate, Caprylic/Capric Triglyceride | Jeen Int'l | 3.0 |
| A | Jeesilc ® DMBF Aqua Base | Dimethicone (and) Cetyl PEG/PPG-10 Dimethicone (and) Bis-Vinyl Dimethicone/Dimethicone Copolymer | Jeen Int'l | 6.0 |
| A | Jeesilc ® PDS1 | Dimethicone | Jeen Int'l | 4.0 |
| A | Mineral Oil | Mineral Oil | Jeen Int'l | 0.5 |
| A | PVPK-30 | Polvinylpyrrolidone | ISP | 4.0 |
| A | BTD 11S2 | Titanium Dioxide (AND) Triethoxycaprylylsilane | Kobo | 2.0 |
| A | Jeecide ® GII | Propylene Glycol, Diazolidinyl Urea, Methyl Paraben, Propyl Paraben | Jeen Int'l | 1.0 |
| B | Kobomica L-25 | MICA | Kobo | 3.0 |
| B | KTZ Bronze | Mica and Titanium Dioxide | Kobo | 5.0 |
| B | Chromatique Cupreous Brown | Mica and Iron Oxide | Impact Color | 2.0 |

Mix Phase A at room temperature. Add Phase B until homogenous.

Formulation Example 36

CPW-BC Lip Paint (J12-25)

| | | | | |
|---|---|---|---|---|
| A | Water | Water | | 61.2 |
| A | Jeesperse CPW-BC | *Theobroma Cacao* (Cocoa) Seed Butter, Beeswax, Yellow Refined, Sodium Polyacrylate | Jeen Int'l | 5.0 |
| A | Shea Butter | Shea (*Butyrospermum Parkii*) Butter | Jeen Int'l | 5.0 |
| A | Coconut Oil | *Cocos Nucifera* (Coconut) Oil | Jeen Int'l | 4.0 |
| A | Jeechem ® CTG | Caprylic/Capric Triglyceride | Jeen Int'l | 4.0 |
| A | Sesame Oil | *Sesamum Indicum* (Sesame) Seed Oil | Jeen Int'l | 2.0 |
| A | Jeecide ® GII | Propylene Glycol, Diazolidinyl Urea, Methyl Paraben, Propyl | Jeen Int'l | 1.0 |
| A | Jeecide ® GII | Propylene Glycol, Diazolidinyl Urea, Methyl Paraben, Propyl Paraben | Jeen Int'l | 1.0 |
| A | *Stevia* | *Eupatorium Rebaudianum Bertoni* Leaf Extract | Fabrichem Inc | 0.1 |
| A | Vanilla Lace Scent | Fragance | Fragance Resources | 0.1 |
| A | Jeesilc ® EM-90 | Cetyl Peg/Ppg-10 Dimethicone | Jeen Int'l | 2.0 |
| B | Performa V 825 | Synthetic Wax | New Phase | 2.5 |
| B | SW40R7C | Synthetic Wax/Red 7 | Kobo | 6.5 |
| B | SW60ER | Synthetic Wax/Red Oxide | Kobo | 0.8 |
| B | SW55EB | Synthetic Wax/Black | Kobo | 0.2 |

Mix Phase A at Room temperature. Add Phase B mix until homogenous.

Formulation Example 37

CPW-BC Lip Paint (J12-25B)

| | | | | |
|---|---|---|---|---|
| A | Water | Water | | 56.2 |
| A | Jeesperse CPW-BC | *Theobroma Cacao* (Cocoa) Seed Butter, Beeswax, Yellow Refined, Sodium Polyacrylate | Jeen Int'l | 10.0 |
| A | Shea Butter | Shea (*Butyrospermum Parkii*) Butter | Jeen Int' | 5.0 |
| A | Coconut Oil | *Cocos Nucifera* (Coconut) Oil | Jeen Intl | 4.0 |
| A | Jeechem ® CTG | Caprylic/Capric Triglyceride | Jeen Int'l | 4.0 |
| A | Sesame Oil | *Sesamum Indicum* (Sesame) Seed Oil | Jeen Int'l | 2.0 |
| A | Jeecide ® GII | Propylene Glycol, Diazolidinyl Urea, Methyl Paraben, Propyl Paraben | Jeen Int'l | 1.0 |
| A | *Stevia* | *Eupatorium Rebaudianum Bertoni* Leaf Extract | Fabrichem Inc | 0.1 |
| A | Vanilla Lace Scent | Fragance | Fragance Resources | 0.1 |
| A | Jeesilc ® EM-90 | Cetyl PEG/PPG-10 Dimethicone | Jeen Int'l | 2.0 |
| B | Performa V 825 | Synthetic Wax | New Phase | 2.5 |
| B | SW40R7C | Synthetic Wax/Red 7 | Kobo | 6.5 |
| B | SW60ER | Synthetic Wax/Red Oxide | Kobo | 0.8 |
| B | SW55EB | Synthetic Wax/Black Oxide | Kobo | 0.2 |
| B | Mica | Mica | Kobo | 2.6 |
| B | KTZ Ultrashimmer Gold | Ultrashimmer Gold | Kobo | 3.0 |

Mix Phase A at Room temperature. Add Phase B mix until homogenous.

Formulation Example 38

CPW-2-Crosspolymer Cream (J12-27 NJM)

| A | DI Water | Distilled Water | | 87.0 |
|---|---|---|---|---|
| A | Jeesperse ® CPW-2-Crosspolymer | Polyethylene, Sodium Polyacrylate, Dimethicone/Vinyl Dimethicone Crosspolymer | Jeen Int'l | 10.0 |
| B | Jeesilc ® PDS-350 | Dimethicone (Polydimethylsiloxane) | Jeen Int'l | 2.0 |
| B | Jeecide ® G-II | Propylene Glycol, Diazolidinyl Urea, Methyl Paraben, Propyl Paraben | Jeen Int'l | 1.0 |

Mix Phase A to room temperature. Add Phase B until homogenous.

Formulation Example 39

CPW-2-Crosspolymer Cream (J12-27ANJM)

| A | DI Water | Distilled Water | | 87.0 |
|---|---|---|---|---|
| A | Jeesperse ® CPW-2-Crosspolymer | Polyethylene, Sodium Polyacrylate, Dimethicone/Vinyl Dimethicone Crosspolymer | Jeen Int'l | 10.0 |
| B | Jeesilc ® DMC-153 | Dimethicone, Dimethiconol | Jeen Int'l | 2.0 |
| B | Jeecide ® G-II | Propylene Glycol, Diazolidinyl Urea, Methyl Paraben, Propyl Paraben | Jeen Int'l | 1.0 |

Mix Phase A to room temperature. Add Phase B until homogenous.

Formulation Example 40

CPW-2-Crosspolymer Cream (J12-27B NJM)

| A | DI Water | Distilled water | | 87.0 |
|---|---|---|---|---|
| A | Jeesperse ® CPW-2-Crosspolymer | Polyethylene, Sodium Polyacrylate, Dimethicone/Vinyl Dimethicone Crosspolymer | Jeen Int'l | 10.0 |
| B | Jeesilc ® DMBF | Dimethicone, Bis-Vinyl Dimethicone/Dimethicone Copolymer, | Jeen Int'l | 2.0 |
| B | Jeecide ® G-II | Propylene Glycol, Diazolidinyl Urea, Methyl Paraben, Propyl Paraben | Jeen Int'l | 1.0 |

Mix Phase A to room temperature. Add Phase B until homogenous.

Formulation Example 41

CPW-2-Crosspolymer Cream (J12-27C NJM)

| A | DI Water | Distilled water | | 87.0 |
|---|---|---|---|---|
| A | Jeesperse ® CPW-2-Crosspolymer | Polyethylene, Sodium Polyacrylate, Dimethicone/Vinyl Dimethicone Crosspolymer | Jeen Int'l | 10.0 |
| B | Jeesilc ® PDS 1.0 | Dimethicone | Jeen Int'l | 2.0 |
| B | Jeecide ® G-II | Propylene Glycol, Diazolidinyl Urea, Methyl Paraben, Propyl Paraben | Jeen Int'l | 1.0 |

Mix Phase A to room temperature. Add Phase B until homogenous.

We claim:

1. A cold process for making an emulsion or hydrogel comprising the step of combining a cold process formulation aid having a wax component with an aqueous medium, at a temperature not exceeding 30° C., wherein the cold process formulation aid is in the form of a powder, a paste, or a semi-solid and consists essentially of: (i) a polymer having an aliphatic backbone and a plurality of pendant groups thereon that are pendant ionic or ionizable groups, and (ii) a wax component selected from the group consisting of natural waxes and synthetic waxes, wherein
   - if the wax is not micronized, the ratio, by weight of the non-micronized wax to the polymer having an aliphatic backbone is from about 60:40 to 80:20, and
   - if the wax is a micronized wax, it has a particle size not exceeding about 50µ and the ratio, by weight, of micronized wax to the polymer having an aliphatic backbone and a plurality of pendant groups thereon that are pendant ionic or ionizable groups is from about 85:15 to 98:2.

2. The cold process of claim 1 wherein the emulsion or hydrogel is a personal care product that is essentially surfactant free and the wax is a natural wax.

3. The cold process of claim 1 wherein a hydrogel or an emulsion is a personal care product that is essentially surfactant free and the micronized wax is a micronized natural wax.

4. The cold process of claim 1 wherein a hydrogel or an emulsion is a personal care product that is essentially surfactant free and the micronized wax is a micronized synthetic wax.

5. A cold process for making a hydrogel or an emulsion comprising the step of combining a cold process formulation aid having a wax component with an aqueous medium, at a temperature not exceeding 30° C., wherein the cold process formulation aid is in the form of a powder, a paste, or a semi-solid and consists essentially of: (i) a polymer having an aliphatic backbone and a plurality of pendant groups thereon that are pendant ionic or ionizable groups, and (ii) a self-emulsifying wax, the ratio, by weight of the self-emulsifying wax to the polymer having an aliphatic backbone and a plurality of pendant groups thereon that are pendant ionic or ionizable groups is from about 70:30 to 98:2.

* * * * *